(12) United States Patent
Hatakeyama et al.

(10) Patent No.: US 6,538,145 B2
(45) Date of Patent: Mar. 25, 2003

(54) 24-HYDROXY VITAMIN D DERIVATIVES

(75) Inventors: Susumi Hatakeyama, Nagasaki (JP); Hiroyoshi Watanabe, Shizuoka (JP); Akira Kawase, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/099,987

(22) Filed: Mar. 19, 2002

(65) Prior Publication Data

US 2002/0094972 A1 Jul. 18, 2002

Related U.S. Application Data

(62) Division of application No. 09/622,813, filed as application No. PCT/JP99/00796 on Feb. 23, 1999, now abandoned.

(30) Foreign Application Priority Data

Feb. 24, 1998 (JP) .............................................. 10-42295

(51) Int. Cl.[7] ...................... A61K 31/593; C07C 401/00
(52) U.S. Cl. ...................... 552/653; 514/167; 514/182; 552/653
(58) Field of Search ...................... 552/653; 514/182, 514/167

(56) References Cited

U.S. PATENT DOCUMENTS 5,945,410 A * 8/1999 DeLuca et al. .............. 514/167
6,277,837 B1 * 8/2001 DeLuca et al. .............. 514/167

OTHER PUBLICATIONS

Posner et al. (J. Med. Chem. 1995, vol. 38, 4529–4537).*
Zhao et al., "Synthesis and Biological Evaluation of some 25,26–epoxy–1α, 24–dihydroxyvitamin $D_3$ Analogues", Bioorganic & Medical Chemistry Letters, vol. 3, No. 9, pp. 1863–1867, 1993.

Baggiolini et al., "Stereocontrolled Total Synthesis of 1α,25–Dihydroxycholecalciferol[1] and 1α,25–Dihydroxyergocalciferol," J. Org. Chem., 1986, 51, pp. 3098–3108.

* cited by examiner

Primary Examiner—Sabiha Qazi
(74) Attorney, Agent, or Firm—Browdy and Neimark PLLC

(57) ABSTRACT

A process for preparing vitamin D derivatives having the following formula:

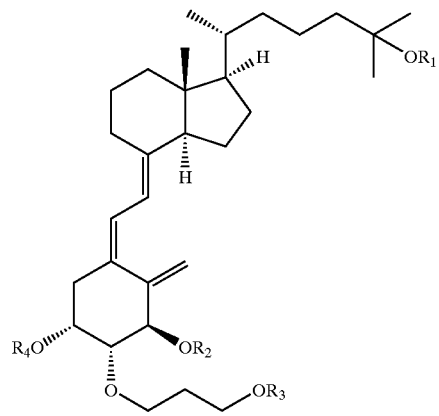

(6)

wherein $R_1$, $R_2$, $R_3$, and $R_4$, which may be the same or different, represent a hydrogen atom or a protecting group, comprising:

Competitive reaction of test compounds to vitamin D receptor from chick intestine reacting a compound of formula (2)
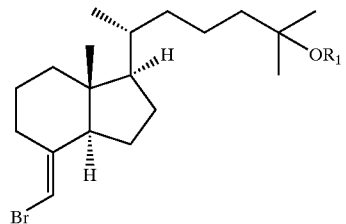 (7)
wherein $R_1$ represents a hydrogen atom or a protecting group, with a compound having the formula (3)
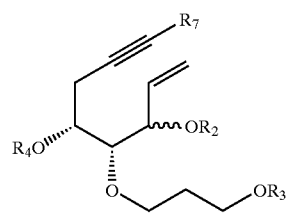 (5)
wherein $R_1$ represents a hydrogen atom and $R_2$, $R_3$, and $R_4$, which are the same or different, represent a hydrogen atom or a protecting group.
2 Claims, 1 Drawing Sheet

24-HYDROXY VITAMIN D DERIVATIVES

This application is a division of Ser. No. 09/622,813, now abandoned, which was been filed under 35 USC 371 as a national stage application of PCT/JP99/00796, filed Feb. 23, 1999.

TECHNICAL FIELD

The present invention relates to vitamin D derivatives having a hydroxy group at 24-position thereof, and particularly relates to vitamin D derivatives having a substituent at 2β position and a hydroxy group at 24-position.

BACKGROUND OF THE INVENTION

Recently, some of the physiological activities of vitamins D have been revealed. It is known that a certain vitamin D, for example, 1α, 25-dihydroxyvitamin $D_3$, exhibits a variety of physiological activities such as a calcium metabolism-controlling activity, a proliferation-inhibiting activity and a differentiation-inducing activity on cells such as tumor cells, and an immune-controlling activity.

However, 1α, 25-dihydroxyvitamin $D_3$ disadvantageously causes hypercalcemia depending on the dose and/or the administration route and thus is not suitable for use as an antitumor agent, a therapeutic agent for rheumatic diseases, etc. In order to isolate such activities of the vitamin D derivatives, numerous vitamin D derivatives have been synthesized these days and their physiological activities were evaluated.

Among numerous vitamin $D_3$ derivatives, some of those which have a substituent at the 2β-position possess physiological activities such as calcium metabolism-controlling activity and differentiation-inducing activity on cells such as tumor cells and are known to be useful as a medicine, such as a therapeutic agent for diseases associated with abnormal calcium metabolism, such as osteoporosis, osteomalacia, etc. and an antitumor agent (Japanese Patent Publication (Kokoku) No. 3-14303, Japanese Patent Publication (Kokai) No. 61-267549 and Japanese Patent Publication (Kokai) No. 6-41059). Among them, 2β-(3-hydroxypropoxy)-1α, 25-dihydroxyvitamin $D_3$ is expected to be of practical use in treating osteoporosis, with a high blood level being able to be maintained for a long duration.

Vitamin $D_3$ derivatives may be synthesized, for example, by epoxidation and then opening the A ring structure of a steroid compound (used as a starting material) so as to introduce the substituent to 2-position (Japanese Patent Publication (Kokai) No. 61-267549) or by coupling the A ring part and the CD ring part of the vitamin D derivative, which parts have been synthesized separately. Japanese Patent Publication (Kokai) No. 6-25039 and Japanese Patent Application No. 9-53316 (published as Japanese Patent Publication (Kokai) No. 10-251183) disclose processes for synthesizing the A ring part of vitamin D derivatives.

As described above, the 2β-(3-hydroxypropoxy)-1α, 25-dihydroxyvitamin $D_3$ has been developed as a useful medicine; at the same time, its metabolites are also under study. With recent progress in the study of 2β-(3-hydroxypropoxy)-1α, 25-dihydroxyvitamin $D_3$ metabolites, it has been suggested that some of the metabolites have their side chain hydroxylated. However, no report has been made concerning the synthesis of a 2β-(3-hydroxypropoxy)-1α, 25-dihydroxyvitamin $D_3$ derivative of which the 24-position is hydroxylated.

DISCLOSURE OF THE INVENTION

One object of the present invention is to provide a novel vitamin D derivative of which 24-position is hydroxylated.

Another object of the present invention is to provide novel intermediates which are useful for synthesizing the above-mentioned novel vitamin D derivative of which 24-position is hydroxylated, more specifically, intermediates corresponding to the A ring part and intermediates corresponding to the C ring part of the vitamin D derivative skeleton.

Still another object of the present invention is to provide a process by which the novel vitamin D derivative of the present invention of which 24-position is hydroxylated is synthesized by using the intermediates of the present invention.

Still another object of the present invention is to provide a process for synthesizing 2β-(3-hydroxypropoxy)-1α, 25-dihydroxyvitamin $D_3$ by using the novel intermediates of the present invention.

With a view to attaining the above-mentioned objects, the inventors of the present invention investigated the various reactions involved in the synthesis of the CD ring part and A ring part of vitamin D skeleton and in the coupling of the CD ring part and the A ring part and, as a result, achieved the synthesis of the desired vitamin $D_3$ derivative having a hydroxy group at 24-position by first synthesizing 1-[4,5-bis(t-butyldimethylsilyloxy)-1,5 -dimethylhexyl]-4-bromomethylene-7a-methyl-octahydro-1H-indene and 3,5-bis(t-butyldimethylsilyloxy)-4-(3-t-butyldimethylsilyloxypropoxy)-1-octen-7-ine,separately as the CD ring part and the A ring part, respectively and coupling them together, thereby completing the present invention.

According to a first aspect of the present invention, there are provided vitamin D derivatives having the general formula (1):

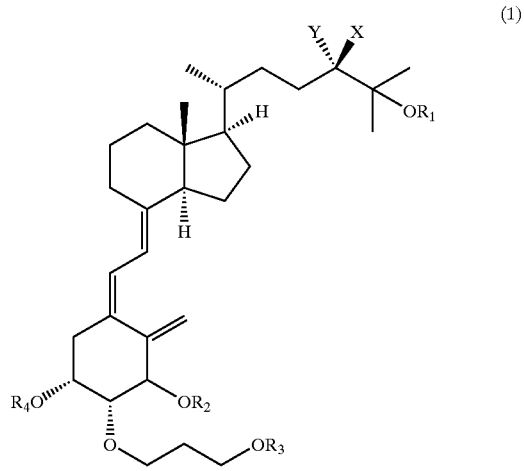

(1)

[wherein $R_1$, $R_2$, $R_3$ and $R_4$, which may be the same or different, represent a hydrogen atom or a protecting group; X and Y represent H or $OR_5$, provided Y is $OR_5$ when X is H and Y is H when X is $OR_5$ (wherein $R_5$ is a hydrogen atom or a protecting group and $R_1$ and $R_5$ may together form a vicinal-diol protecting group)].

Preferably, the 1-position of the general formula (1) is in R-configuration.

According to a second aspect of the present invention, there are provided compounds having the general formula (2):

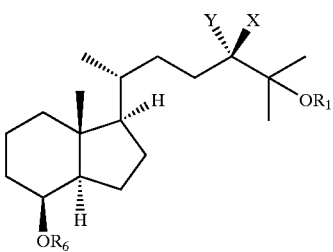

(2)

[wherein $R_1$ and $R_6$, which may be the same or different, represent a hydrogen atom or a protecting group; X and Y represent H or $OR_5$, provided Y is $OR_5$ when X is H and Y is H when X is $OR_5$ (wherein $R_5$ represents a hydrogen atom or a protecting group and $R_1$ and $R_5$ may together form a vicinal-diol protecting group)];

compounds having the general formula (3):

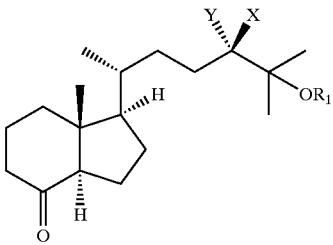

(3)

[wherein $R_1$ represents a hydrogen atom or a protecting group; X and Y represent H or $OR_5$, provided Y is $OR_5$ when X is H and Y is H when X is $OR_5$ (wherein $R_5$ represents a hydrogen atom or a protecting group and $R_1$ and $R_5$ may together form a vicinal-diol protecting group)]; and compounds having the formula (4):

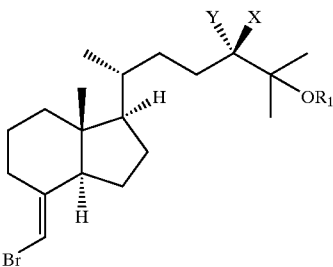

(4)

[wherein $R_1$ represents a hydrogen atom or a protecting group; X and Y represent H or $OR_5$, provided Y is $OR_5$ when X is H and Y is H when X is $OR_5$ (wherein $R_5$ represents a hydrogen atom or a protecting group and $R_1$ and $R_5$ may together form a vicinal-diol protecting group)]. These compounds are useful as intermediates for the synthesis of compounds of the general formula (1).

According to a third aspect of the present invention, there are provided compounds having the general formula (5):

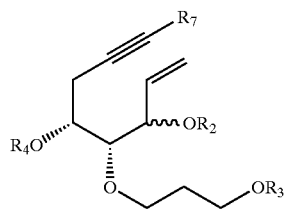

(5)

(wherein $R_7$ represents a trimethylsilyl group or a hydrogen atom; and $R_2$, $R_3$ and $R_4$, which are the same or different, represent a hydrogen atom or a protecting group). These compounds are useful as intermediates for the synthesis of compounds of the general formula (1).

According to a fourth aspect of the present invention, there is provided a process for preparing vitamin D derivatives having the general formula (1):

(1)

[wherein $R_1$, $R_2$, $R_3$ and $R_4$, which may be the same or different, represent a hydrogen atom or a protecting group; X and Y represent H or $OR_5$, provided Y is $OR_5$ when X is H and Y is H when X is $OR_5$ (wherein $R_5$ is a hydrogen atom or a protecting group and $R_1$ and $R_5$ may together form a vicinal-diol protecting group)] comprising:

reacting a compound having the general formula (4):

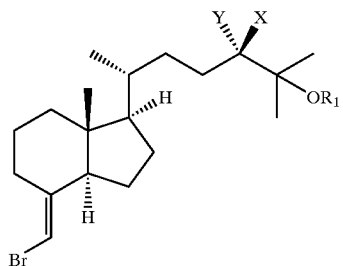

(4)

[wherein $R_1$ represents a hydrogen atom or a protecting group; X and Y represent H or $OR_5$, provided Y is $OR_5$ when X is H and Y is H when X is $OR_5$ (wherein $R_5$ represents a hydrogen atom or a protecting group and $R_1$ and $R_5$ may together form a vicinal-diol protecting group)]

with a compound of the general formula (5):

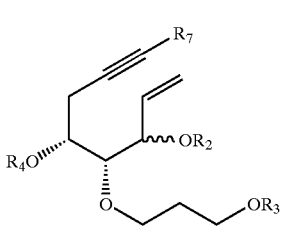

(wherein $R_7$ represents a hydrogen atom; and $R_2$, $R_3$ and $R_4$, which are the same or different, represent a hydrogen atom or a protecting group).

In the above process, the $OR_2$ group at the 3-position of the compound having the general formula (5) is in R-configuration and the 1-position of the compound having the general formula (1) is in R-configuration.

According to a fifth aspect of the present invention, there are provided a process for preparing vitamin D derivatives having the general formula (6):

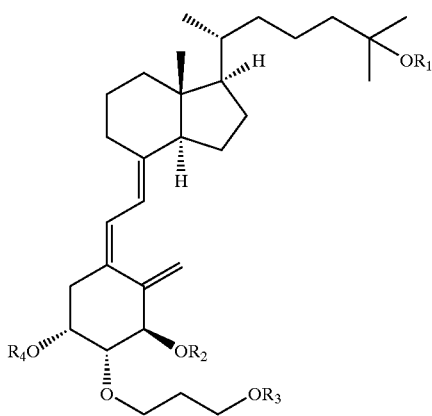

(wherein $R_1$, $R_2$, $R_3$ and $R_4$, which may be the same or different, represent a hydrogen atom or a protecting group) comprising:

reacting a compound having the general formula (7):

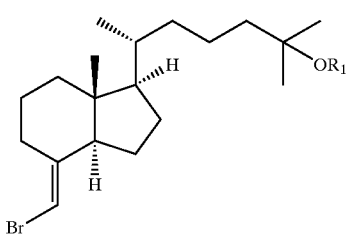

(wherein $R_1$ represents a hydrogen atom or a protecting group)

with a compound having the general formula (5):

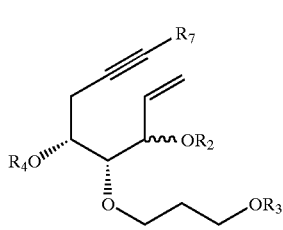

(wherein $R_7$ represents a hydrogen atom; and $R_2$, $R_3$ and $R_4$, which are the same or different, represent a hydrogen atom or a protecting group).

According to a sixth aspect of the present invention, there are provided pharmaceutical compositions comprising a vitamin D derivative having the general formula (1):

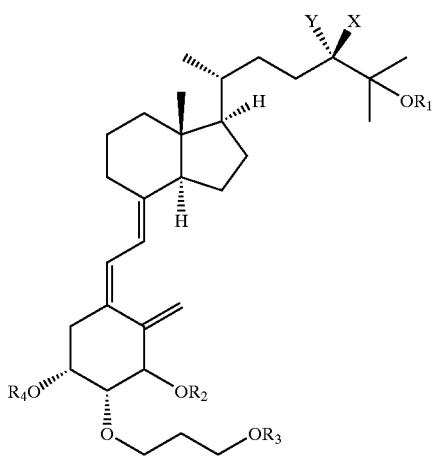

[wherein $R_1$, $R_2$, $R_3$ and $R_4$, which may be the same or different, represent a hydrogen atom or a protecting group; X and Y represent H or $OR_5$, provided Y is $OR_5$ when X is H and Y is H when X is $OR_5$ (wherein $R_5$ is a hydrogen atom or a protecting group and $R_1$ and $R_5$ may together form a vicinal-diol protecting group)].

The pharmaceutical compositions of the present invention can be used, for example, as a therapeutic agent for diseases associated with abnormal calcium metabolism or an antitumor agent.

BEST MODE FOR CARRYING OUT THE INVENTION

Figure 1:
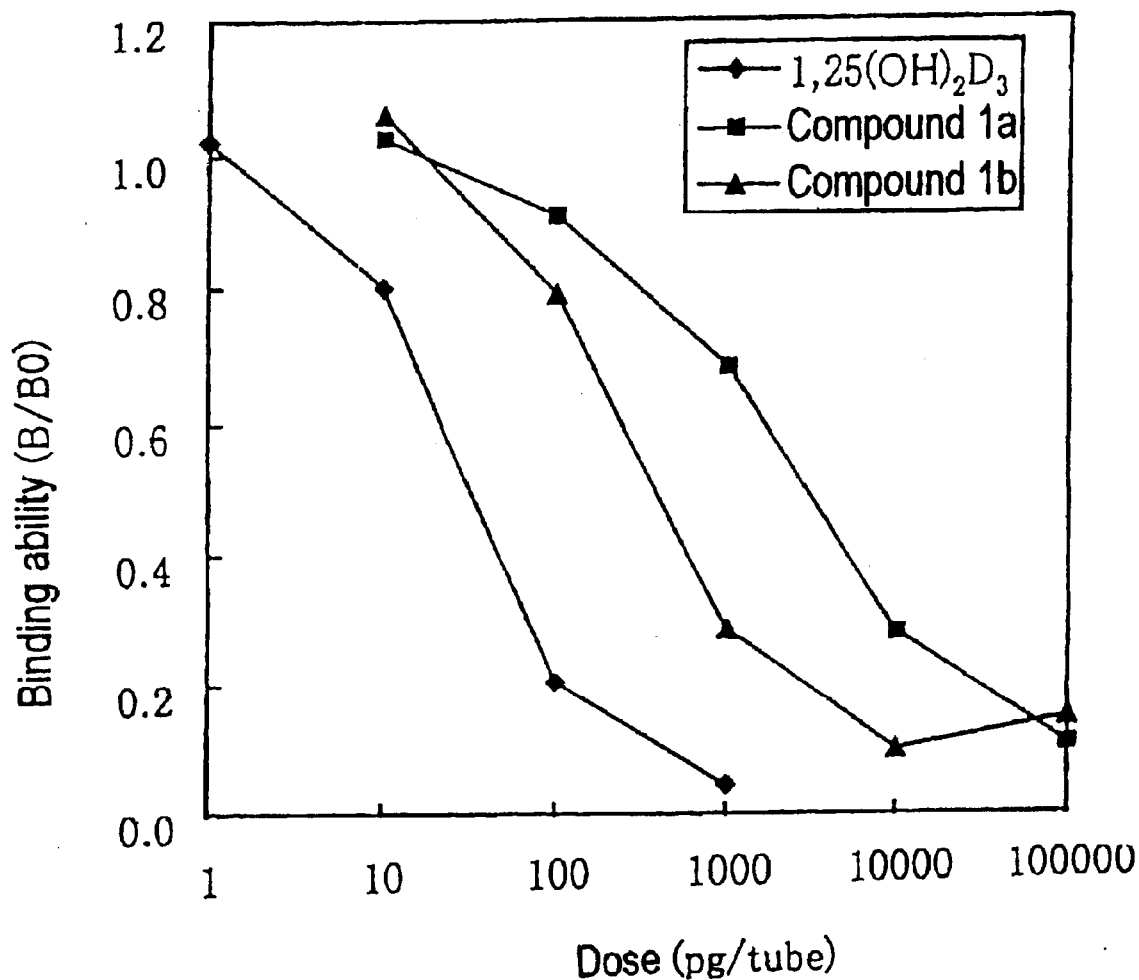
FIG. 1 is a graph showing the affinity of the compounds of the present invention for the vitamin D receptor.

The following are detailed embodiments of the present invention and specific methods for carrying it out.

As used herein, $R_1$ to $R_6$ each represent a hydrogen atom or a protecting group. "Protecting group" refers to a hydroxy group protecting group and includes any protecting groups removable by conventional deprotecting means (e.g. hydrolysis, oxidative cleavage, reductive cleavage and hydrogenlysis) substantially free of harmful effects on any other portions of the molecule.

Non-limiting examples of the protecting groups are as follows:

(I) an acyl group represented by $R^aCO—$ (wherein $R^a$ is a hydrogen atom, a C1–C6 alkyl group, a C1–C6 haloalkyl group or an aryl group); for example, formyl, acetyl, propionyl, butyryl, isobutyryl, valeryl, isovaleryl, pivaloyl, caproyl, benzoyl, trifluoroacetyl, etc.

(II) an alkoxycarbonyl group represented by $R^bOCO—$ (wherein $R^b$ is a C1–C6 alkyl group, a C1–C6 alkenyl group, a C7–C9 aralkyl group, or an aryl group); for example, methoxycarbonyl, ethoxycarbonyl, propoxycarbonyl, isopropoxycarbonyl, allyloxycarbonyl, benzyloxycarbonyl, phenoxycarbonyl, etc.

(III) a trisubstituted silyl group represented by the following formula:

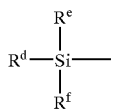

(wherein $R^d$, $R^e$ and $R^f$, which are the same or different, represent a C1–C6 alkyl group, an aryl group or a C7–C9 aralkyl group); for example, trimethylsilyl, triethylsilyl, triisopropylsilyl, t-butyldimethylsilyl, t-butyldiphenylsilyl, tribenzylsilyl, etc.

(IV) a 1-alkoxy or 1-mercaptoalkyl group represented by the following formula:

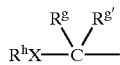

{wherein X represents an oxygen atom or a sulfur atom and $R^g$ and $R^{g'}$ each represent a hydrogen atom or a C1–C6 alkyl group; $R^h$ is a substituted or unsubstituted C1–C6 alkyl group [examples of the substituent are a lower alkoxy group, a halogen atom such as chlorine, an alkyl substituted silyl group (e.g. trimethylsilyl group) and a phenyl group which may be substituted with an alkoxy group, a halogen atom, etc.]}; for example, methoxymethyl, methoxyethoxymethyl, 1-ethoxyethyl, methoxyisopropyl, methylthiomethyl, t-butylthiomethyl, β-trichloroethyloxymethyl, trimethylsilylethoxymethyl, p-methoxybenzyloxymethyl, p-chlorobenzyloxymethyl, etc.

(V) a 2-oxacycloalkyl group represented by the following formula:

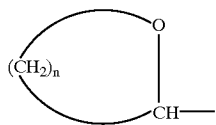

(wherein n is an integer of 3 to 6); for example, a tetrahydrofuralyl group, a tetrahydropyranyl group, etc. (VI) an aralkyl group such as a benzyl group:

Alternatively, $R_1$ and $R_5$ may together form a vicinal-diol protecting group according to the present invention.

Examples of the vicinal-diol protecting group include protecting groups in the acetal or ketal form and in the orthoester form. Specific examples of the protecting group in the acetal or ketal form include a methylene group, a diphenylmethylene group, an ethylidene group, a 1-t-butylethylidene group, a 1-phenylethylidene group, a (4-methoxyphenyl) ethylidene group, a 2,2,2-trichloroethylidene group, an isopropylidene group, a cyclopentylidene group, a cyclohexylidene group, a cycloheptylidene group, a benzylidene group, a p-methoxybenzylidene group, a 2,4-dimethoxybenzylidene group, a 3,4-dimethoxybenzylidene group, a 2-nitrobenzylidene group, etc. and specific examples of the protecting group in the orthoester form include a methoxymethylene group, an ethoxymethylene group, a dimethoxymethylene group, a 1-methoxyethylidene group, a 1-ethoxyethylidene group, a 1,2-dimethoxyethylidene group, an α-methoxybenzylidene group, a 1-(N,N-dimethylamino) ethylidene group, an α-(N,N-dimethylamino)benzylidene group, a 2-oxacyclopentylidene group, etc.

The compounds having the general formula (1) of the present invention are novel and can be synthesized, for example, by coupling an A ring part and a CD ring part of vitamin D derivatives after they have been separately synthesized beforehand.

As the A ring part, the compounds of the general formula (5) may be used and these compounds are also novel and useful as intermediates for the synthesis of the compounds of the general formula (1) of the present invention. The compound of the general formula (5) may be synthesized as typically shown in Example 21 to be described later: first, acetylene is added to 1,2-epoxy-4-pivaloyloxy-3-(3'-pivaloyloxypropoxy)-5-hexene which is mentioned in Japanese Patent Application No. 9-53316 (published as Japanese Patent Publication (Kokai) No. 10-251183 the whole content of which is incorporated herein by reference), and then appropriately adding and/or removing and/or substituting with a protecting group. The reaction of acetylene addition can be carried out as follows: a compound having a metal-acetylene-protecting group structure is produced by adding a solution of a metallic alkyl (e.g. n-butyl lithium) in solvent to a solution of acetylene having a protecting group (e.g. trimethylsilyl group) in an inert solvent (e.g. tetrahydrofuran (THF)) solution and then a solution of 1,2-epoxy-4-pivaloyloxy-3-(3'-pivaloyloxypropoxy)-5-hexene in solvent is added thereto. The reaction temperature can appropriately be selected according to the type of the solvent and other factors; generally, −78° C. to 0° C,. preferably, −78° C. to −50° C. The reaction time can also be selected appropriately; generally, 1 to 5 hours, preferably, 2 to 3 hours.

The compounds of the general formula (4) can be used as the CD part and can be synthesized from a compound of the general formula (2) via a compound of the general formula (3). The compounds of the general formula (2), (3) and (4) are novel and useful as intermediates for the synthesis of the compounds of the general formula (1) of the present invention and various vitamin D derivatives having a hydroxy group at 24-position thereof.

The compound of the general formula (2) may be synthesized as typically shown in Examples 1 to 15 to be described later: with a sulfone obtainable from vitamin $D_2$ via 5 steps (X. Zhao, P. De Clercq, M. Vandewalle, K. Allewaert, H. Van Baelen and R. Bouillon, Bioorganic & Medicinal Chemistry Letters, 3, 1863 (1993)) being used as a starting compound, the side chain part is constructed in accordance with the method of Schik et al. (E. Schroetter, B. Schoenecker, U. Hauschild, P. Droescher and H. Schick, Synthesis, 193 (1990)) followed by protecting and deprotecting steps.

A compound of the general formula (2) is oxidized to convert the hydroxy group at 4-position to an oxo group so as to give a compound of the general formula (3). Such oxidization can be typically carried out under the conditions described in Examples 16, 17 and 18 to be given later. Under such oxidizing conditions, α-epimers of ketone are not produced at all. Epimers may be produced under other conditions such as the use of PCC.

A compound of the general formula (4) is obtainable by converting the oxo group at 4-position of the compound of the general formula (3) to a bromomethylene group under conditions such as those described in Examples 19 and 20. In this reaction, the bromomethylene group is constructed in a desired E configuration (B. M. Trost, J. Dumas and M. Villa, Journal of the American Chemical Society, 114, 9836–9845 (1992)).

The thus obtained compound of the general formula (5) and compound of the general formula (4), which correspond to the A ring part and the CD ring part, respectively, are coupled, for example, under the conditions described in Example 22 to give a vitamin D derivative having an optionally protected hydroxy group at 24-position.

The coupling reaction may be carried out by subjecting the above-mentioned compounds to reaction in a solvent such as THF, acetonitrile, benzene, toluene, xylene, dimethylsulfoxide, N,N-dimethylformamide, N,N-dimethylacetamide, etc. These solvents may be used either alone or in admixture. Toluene is preferred among these solvents. Although not being particularly limited, the reaction temperature is generally at 25 to 140° C., preferably at 60 to 110° C. Although not being particularly limited, the reaction time ranges generally from 2 to 12 hours, preferably from 3 to 6 hours.

Active vitamin D derivatives can be obtained by removing the hydroxy group protecting group, after the coupling reaction as required. Such addition and removal of protecting groups are well known to those skilled in the art.

According to the present invention, there is provided a process by which 2β-(3-hydroxypropoxy)-1α,25-dihydroxyvitamin $D_3$ (this compound per se is known) which possesses useful physiological activities is synthesized by using the compound of the general formula (5) corresponding to the A ring part of the vitamin D derivatives. Specifically, the desired product can be obtained by coupling the compound of the general formula (5) with the compound of the general formula (7). Conditions for the coupling reaction are similar to those described for the coupling reaction between the compound of the general formula (5) and the compound of the general formula (4) and these can be appropriately selected by those skilled in the art.

According to the present invention, pharmaceutical compositions comprising a compound of the general formula (1) are provided. The dosage form of the pharmaceutical compositions of the present invention is not particularly limited, and any form such as tablets, capsules, dispersions, solutions, suspensions and emulsions may be employed depending on the usage and other factors. The pharmaceutical compositions of the present invention comprise a therapeutically effective amount of a compound of the general formula (1) and may optionally contain a pharmaceutically acceptable carrier or excipient.

The pharmaceutical compositions of the present invention may be administered orally or parenterally. In the case of parenteral administration, any administration route, for example, intravenous, intramuscular, intraperitoneal or external application route may be employed.

The dose of the pharmaceutical compositions of the present invention is not particularly limited, either, and can be appropriately selected depending on, for example, the body weight or sex of the patient, the conditions of the disease. In general, each patient may receive 0.001 μg/kg/day to 1000 μg/kg/day, preferably 0.01 μg/kg/day to 100 μg/kg/day, more preferably 0.1 μg/kg/day to 10 μg/kg/day. The frequency of administration is not particularly limited, either. The above-mentioned dose may be administered either singly per day or in several portions a day. The duration of administration may range from several days to several weeks or from several weeks to several months.

The present invention will now be illustrated in greater detail with reference to the following Examples, but it should be understood that the present invention is by no means limited thereto.

EXAMPLES

Example 1

Synthesis of [3a(R)]-4(S)-acetyloxy-7a(R)-methyl-1(R)-[1(S)-methyl-2-phenylsulfonylethyl]-octahydro-1H-indene (Compound 5)

Under cooling with ice, acetic anhydride (188 μl, 1.99 mmol) was added to a solution of [3a(R)]-4(S)-hydroxy-7a(R)-methyl-1(R)-[1(S)-methyl-2-phenylsulfonylethyl]-octahydro-1H-indene (compound 4; 334 mg, 994 μmol), pyridine (200 μl) and N,N-dimethylaminopyridine (DMAP) (18 mg) in dichloromethane (20 ml), followed by stirring for 16 hours at room temperature under argon atmosphere. The reaction mixture was poured into diluted hydrochloric acid, extracted with dichloromethane and washed with a saturated solution of sodium hydrogencarbonate ($NaHCO_3$). The organic layer was dried over magnesium sulfate ($MgSO_4$) and distilled to remove the solvent under reduced pressure; the resulting residue was purified by flash column chromatography (40% ethyl acetate/hexane) to give the titled compound (368 mg, 98%) as a colorless oil.

$^1$H NMR: δ 0.86(3H,s), 1.20(3H, d, J=6.8 Hz), 2.03(3H, s), 2.84(1H, dd, J=14.1, 9.8 Hz), 3.11(1H, d, J=14.1 Hz), 5.12(1H, brs), 7.52–7.96(5H, m);

IR (neat) cm$^{-1}$. 2945, 1735, 1310, 1250, 1150;

MS(m/z): 336 (M$^+$-Ac), 135 (100%);

UV λ max nm: 270, 263, 257, 217.

Example 2

Synthesis of [3a(R)]-1(R)-[4(R),5-dihydroxy-1(S),5-dimethyl-2-phenylsulfonylhexyl]-4(S)-hydroxy-7a(R)-methyl-octahydro-1H-indene (Compound 7a)

Under argon atmosphere at −20° C., n-butyllithium (1.63 M, 2.3 ml, 3.75 mmol) was added dropwise to a solution of [3a(R)]-4(S)-acetyloxy-7a(R)-methyl-1(R)-[1(S)-methyl-2-phenylsulfonylethyl]-octahydro-1H-indene (160 mg, 423 μmol) obtained in Example 1 and 2(R),3-dihydroxy-3-methyl-1 -p-toluenesulfonyloxybutane (R. Dumont and H. Pfander, Helvetica Chimica Acta, 66, 814 (1983) and references cited therein) (232 mg, 847 μmol) in THF (15 ml), followed by stirring for 2 hours at the same temperature. The reaction mixture was poured into a saturated aqueous solution of ammonium chloride, extracted twice with ethyl acetate and washed with saturated aqueous sodium chloride. The organic layer was dried over magnesium sulfate ($MgSO_4$) and distilled under reduced pressure to remove the solvent; the resulting residue was purified by flash column chromatography (ethanol:dichloromethane=0.3:5) to give the titled compound (131 mg, 71%) as colorless foam.

$^1$H NMR: δ 0.67(3H,s), 0.96(3H, d, J=6.8 Hz), 1.20(3H, s), 1.26(3H,s), 3.51(1H, d, J=10.2 Hz), 3.81(1H, brd, J=11.7 Hz), 4.00(1H, brs), 7.52–7.94(5H,m);

IR (neat) cm$^{-1}$: 3500(br), 2935, 1300, 1280, 1135;

MS(m/z): 439(M$^+$+1), 71(100%);

UV λ max nm: 271, 263, 257, 216.

Example 3

Synthesis of [3a(R)]-1(R)-[4(S),5-dihydroxy-1(S),5-dimethyl-2-phenylsulfonylhexyl]-4(S)-hydroxy-7a (R)-methyl-octahydro-1H-indene (Compound 7b)

The same procedure as in Example 2 was repeated using [3a(R)]-4(S)-hydroxy-7a(R)-methyl-1(R)-[1(S)-methyl-2-phenylsulfonylethyl]-octahydro-1H-indene (compound 4; 305 mg, 908 µmol), 2(S),3-dihydroxy-3-methyl-1-paratoluene-sulfonyloxybutane (R. Dumont and H. Pfander, Helvetica Chimica Acta, 66, 814 (1983) and references cited therein) (compound 6b; 249 mg, 909 µmol), THF (20 ml) and n-butyl lithium (1.69 M, 4.3 ml, 7.27 mmol), except that a mixture of ethyl acetate:hexane=4:1 was employed as the solvent for column chromatography. The titled compound was obtained as a colorless oil (110 mg, 28%).

$^1$H NMR: δ 0.69(3H,s), 1.05(3H, d, J=6.6 Hz), 1.20(3H, s), 1.25(3H,s), 3.35(1H, t, J=5.1 Hz), 3.45(1H,brs), 4.01(1H, brs), 7.53–7.94(5H, m);

IR (neat) cm$^{-1}$: 3460(br), 2925, 1280, 1135, 1075;

MS(m/z): 439(M$^+$+1), 60 (100%).

Example 4

Synthesis of [3a(R)]-1(R)-[4(R),5-dihydroxy-1(S),5-dimethylhexyl]-4(S)-hydroxy-7a(R)-methyl-octahydro-1H-indene (Compound 8a)

Sodium amalgam (5%, 5.01 g, 10.9 mmol) was added to a solution in THF (5.5 ml) and methanol (3.5 ml) of the [3a(R)]-1(R)-[4(R),5-dihydroxy-1(S),5-dimethyl-2-phenylsulfonylhexyl]-4(S)-hydroxy-7a(R)-methyl-octahydro-1H-indene (compound 7a;104 mg, 237 µmol) obtained in Example 2 followed by stirring for 15 hours at room temperature. Methanol (5.4 ml) and water (5.4 ml) were added to the reaction solution, followed by stirring for further 30 min. After removing the amalgam by decantation, the reaction solution was poured into a saturated aqueous solution of ammonium chloride, extracted twice with ethyl acetate and washed with brine. The organic layer was dried over magnesium sulfate and distilled under reduced pressure to remove the solvent; the resulting residue was purified by flash column chromatography (ethanol:dichloromethane=0.3:5) to give the titled compound (68 mg, 96%) as colorless foam.

$^1$H NMR: δ 0.91(3H, d, J=6.3 Hz), 0.94(3H, s), 1.21(3H, s), 1.24(3H, s), 3.33(1H, brt, J=5.4 Hz), 4.08(1H, brs);

IR (neat) cm$^{-1}$: 3400(br), 2930;

MS(m/z): 298(M$^+$), 135(100%).

Example 5

Synthesis of [3a(R)]-1(R)-[4(S),5-dihydroxy-1(S),5-dimethylhexyl]-4(S)-hydroxy-7a(R)-methyl-octahydro-1H-indene (Compound 8b)

The same procedure as in Example 4 was repeated using the [3a(R)]-1(R)-[4(S),5-dihydroxy-1(S),5-dimethyl-2-phenylsulfonylhexyl]-4(S)-hydroxy-7a(R)-methyl-octahydro-1H-indene (compound 7b; 216 mg, 493 µmol) obtained in Example 3, THF (12 ml), methanol (7.5 ml) and sodium amalgam (5%, 12.4 g, 27.0 mmol). The titled compound was obtained as a colorless oil (100 mg, 68%).

$^1$H NMR: δ 0.92(3H, d, J=6.6 Hz), 0.93(3H, s), 1.16(3H, s), 1.21(3H, s), 3.27(1H, dd, J=10.2, 2.0 Hz), 4.07(1H, brd, J=2.6 Hz);

IR (neat) cm$^{-1}$: 3400(br), 2930;

MS(m/z): 280(M$^+$—H$_2$O), 60(100%).

Example 6

Synthesis of [3a(R)]-4(S)-hydroxy-7a(R)-methyl-1(R)-[1(S)-methyl-3-[2,2,4,4-tetramethyl-1,3-dioxolane-2 (R)-yl]propyl]-octahydro-1H-indene (Compound 9a)

P-toluenesulfonic acid (TsOH) (6.5 mg, 34.2 µmol) was added to a solution in acetone (19.5 ml) of the [3a(R)]-1(R)-[4(R),5-dihydroxy-1(S),5-dimethylhexyl]-4(S)-hydroxy-7a (R)-methyl-octahydro-1H-indene (compound 8a; 86 mg, 289 µmol) obtained in Example 4 and 2,2-dimethoxypropane (DMP, 2.93 g, 28.1 mmol), followed by stirring for 15 hours at room temperature under argon atmosphere. The reaction mixture was mixed with sodium hydrogencarbonate (10 mg), concentrated under reduced pressure and extracted twice with dichloromethane. The organic layer was dried over magnesium sulfate and distilled under reduced pressure to remove the solvent; the resulting residue was purified by flash column chromatography (ethanol:dichloromethane=0.2:5) to give a crude form of the titled compound (107 mg) as colorless prisms which were used in the following step without further purification.

1H NMR: δ 0.93(3H, d, J=5.3 Hz), 0.95(3H, s), 1.10(3H, s), 1.25(3H, s), 1.33(3H, s), 1.42(3H, s), 3.64(1H, dd, J=8.5, 3.7 Hz), 4.08(1H, brd, J=2.4 Hz);

IR (KBr) cm$^{-1}$: 3485(br), 2920;

MS(m/z): 338(M$^+$), 323(100%).

Example 7

Synthesis of [3a(R)]-4(S)-hydroxy-7a(R)-methyl-1(R)-[1(S)-methyl-3-[2,2,4,4-tetramethyl-1,3-dioxolan-2 (S)-yl]propyl]-octahydro-1H-indene (Compound 9b)

The same procedure as in Example 6 was repeated using the [3a(R)]-1(R)-[4(S),5-dihydroxy-1(S),5-dimethylhexyl]-4(S)-hydroxy-7a(R)-methyl-octahydro-1H-indene (compound 8b; 100 mg, 289 µmol) obtained in Example 5, 2,2-dimethoxypropane (3.8 g, 36.5 mmol), acetone (23 ml), TsOH (15 mg, 78.9 µmol) and sodium hydrogencarbonate (20 mg). The titled compound was obtained as a colorless oil (76 mg, 67%).

$^1$H NMR: δ 0.93(3H, d, J=6.3 Hz), 0.94(3H, s), 1.10(3H, s), 1.25(3H, s), 1.33(3H, s), 1.41(3H, s), 3.61(1H, dd, J=6.9, 5.9 Hz), 4.08(1H, brs);

IR (neat) cm$^{-1}$: 3520(br), 2930;

MS(m/z): 323(M$^+$-Me, 100%).

Example 8

Synthesis of [3a(R)]-4(S)-acetyloxy-1(R)-[1 (S)-methyl-3-[2,2,4,4-tetramethyl-1,3-dioxolan-2(R)-yl] propyl]-7a(R)-methyl-octahydro-1H-indene (Compound 10a)

Acetic anhydride (120 µl, 1.27 mmol) was added to a solution in dichloromethane (10 ml) of the crude [3a(R)]-4 (S)-hydroxy-7a(R)-methyl-1(R)-[1(S)-methyl-3-[2,2,4,4-tetramethyl-1,3-dioxolan-2(R)-yl]propyl]-octahydro-1H-indene (compound 9a; 107 mg) obtained in Example 6, pyridine (128 µl) and DMAP (7 mg), followed by stirring for 4 hours at room temperature under argon atmosphere. The reaction mixture was poured into diluted hydrochloric acid, extracted with dichloromethane and washed with a saturated sodium carbonate solution. The organic layer was dried over magnesium sulfate and distilled under reduced pressure to remove the solvent; the resulting residue was purified by flash column chromatography (15% ethyl acetate/hexane) to give a crude form of the titled compound (91 mg, 83% yield from [3a(R)]-1(R)-[4(R),5-dihydroxy-1(S),5-dimethylhexyl]-4(S)-hydroxy-7a(R)-methyl-octahydro-1H-indene) as a colorless oil.

$^1$H NMR: δ 0.89(3H, s), 0.95(3H, d, J=6.3 Hz), 1.10(3H, s), 1.25(3H, s), 1.33(3H, s), 1.42(3H, s), 2.04(3H, s), 3.64 (1H, dd, J=8.8, 2.9 Hz), 5.16 (1H, brs);

IR(neat)cm$^{-1}$:2940, 1735:

MS(m/z) :365 (M$^+$-Me, 100%).

Example 9

Synthesis of [3a(R)]-4(S)-acetyloxy-1(R)-[1 (S)-methyl-3-[2,2,4,4-tetramethyl-1,3-dioxolan-2(S)-yl] propyl]-7a(R)-methyl-octahydro-1H-indene (compound 10b)

The same procedure as in Example 8 was repeated using the [3a(R)]-4(S)-hydroxy-7a(R)-methyl-1(R)-[1(S)-methyl-3 -[2,2,4,4-tetramethyl-1,3-dioxolan-2(S)-yl] propyl]-octahydro-1H-indene (compound 9b; 76 mg, 225 μmol) obtained in Example 7, pyridine (500 μl), DMAP (3 mg), dichloromethane (3 ml) and acetic anhydride (250 μl, 2.64 mmol) to give the titled compound (82 mg, 96%) as a pale yellow oil.

$^1$H NMR: δ 0.89(3H, s), 0.94(3H, d, J=6.6 Hz), 1.10(3H, s), 1.25(3H, s), 1.33(3H, s), 1.41(3H, s), 2.04(3H, s), 3.61 (1H, t, J=6.3 Hz), 5.15(1H, brs);

IR (neat) cm$^{-1}$: 2930, 1735;

MS(m/z): 365(M$^+$-Me,100%).

Example 10

Synthesis of [3a(R)]-4(S)-acetyloxy-1(R)-[4(R),5 -dihydroxy-1(S),5-dimethylhexyl]-7a(R)-methyl-octahydro-1H-indene (Compound 11a)

One-percent iodine/methanol (2 ml) was added to the [3a(R)]-4(S)-acetyloxy-1(R)-[1(S)-methyl-3-[2,2,4,4 -tetramethyl-1,3-dioxolan-2(R)-yl]propyl]-7a(R)-methyl-octahydro-1H-indene (compound 10a; 46 mg, 121 μmol) obtained in Example 8, followed by heating under reflux for 4.5 hours. The reaction mixture was poured into a solution of 10% sodium thiosulfate (Na$_2$S$_2$O$_3$), concentrated under reduced pressure, extracted with ethyl acetate and washed twice with water. The organic layer was dried over magnesium sulfate and distilled under reduced pressure to remove the solvent; the resulting residue was purified by flash column chromatography (40% ethyl acetate/hexane) to give the titled compound (25 mg, 61%) as a colorless oil.

$^1$H NMR: δ 0.89(3H, s), 0.92(3H, d, J=6.6 Hz), 1.16(3H, s), 1.21(3H, s), 2.04(3H, s), 3.32(1H, brt, J=5.9 Hz), 5.14 (1H, brs);

IR (neat) cm$^{-1}$: 3455(br), 2930, 1735;

MS(m/z): 280(M$^+$—Ac—H$_2$O), 59(100%).

Example 11

Synthesis of [3a(R)]-4(S)-acetyloxy-1(R)-[4(S),5 -dihydroxy-1(S),5-dimethylhexyl]-7a(R)-methyl-octahydro-1H-indene (Compound 11b)

A mixture of the [3a(R)]-4(S)-acetyloxy-1(R)-[1 (S)-methyl-3-[2,2,4,4-tetramethyl-1,3-dioxolan-2(S)-yl] propyl]-7a(R)-methyl-octahydro-1H-indene (compound 10b; 34 mg, 89.5 μmol) obtained in Example 9, acetic acid (240 μl), water (1.99 ml) and ethanol (2.6 ml) was stirred at 70° C. for 5 days. The reaction mixture was poured into a saturated sodium hydrogencarbonate solution, extracted twice with ethyl acetate and washed with brine. The organic layer was dried over magnesium sulfate and distilled under reduced pressure to remove the solvent; the resulting residue was purified by flash column chromatography (40% ethyl acetate/hexane) to give the titled compound (25 mg, 83%) as a colorless oil.

$^1$H NMR: δ 0.88(3H, s), 0.93(3H, d, J=6.6 Hz), 1.16(3H, s), 1.22(3H, s), 2.04(3H, s), 3.23–3.32(1H, m), 5.15(1H, brs);

IR (neat) cm$^{-1}$: 3460(br), 2935, 1730:

MS(m/z): 340(M$^+$), 135(100%).

Example 12

Synthesis of [3a(R)]-4(S)-acetyloxy-1(R)-[4(R),5 -bis(t-butyldimethylsilyloxy)-1(S),5-dimethylhexyl]-7a (R)-methyl-octahydro-1H-indene (Compound 12a)

Under cooling with ice, t-butyldimethylsilyl-trifluoromethanesulfonate (TBSOTf) (466 μl, 2.03 mmol) was added to a solution in dichloromethane (10 ml) of the [3a(R)]-4(S)-acetyloxy-1(R)-[4(R),5-dihydroxy-1(S),5 -dimethylhexyl]-7a(R)-methyl-octahydro-1H-indene (compound 11a; 46 mg, 135 μmol) obtained in Example 10, and 2,6 -lutidine (355 μl, 3.03 mmol), followed by stirring at room temperature for 1.5 hours. The reaction mixture was poured into ice-cooled 1N hydrochloric acid, extracted with dichloromethane and washed with saturated sodium carbonate solution. The organic layer was dried over magnesium sulfate and distilled under reduced pressure to remove the solvent; the resulting residue was purified by flash column chromatography (6% ethyl acetate/hexane) to give the titled compound (71 mg, 92%) as a colorless oil.

$^1$H NMR: δ 0.04(3H, s), 0.06(3H, s), 0.07(3H, s), 0.08 (3H, s), 0.86(9H, s), 0.89(9H, s), 1.11(3H, s), 1.19(3H, s), 2.04(3H, s), 3.22(1H, brs), 5.15(1H, brs);

IR (neat) cm$^{-1}$: 2945, 1745:

MS(m/z): 553(M$^+$-Me), 173(100%).

Example 13

Synthesis of [3a(R)]-4(S)-acetyloxy-1(R)-[4(S),5 -bis(t-butyldimethylsilyloxy)-1(S),5-dimethylhexyl]-7a (R)-methyl-octahydro-1H-indene (Compound 12b)

The same procedure as in Example 12 was repeated using the [3a(R)]-4(S)-acetyloxy-1(R)-[4(S),5-dihydroxy-1(S),5 -dimethylhexyl]-7a(R)-methyl-octahydro-1H-indene (compound 11b; 31 mg, 91.2 μmol) obtained in Example 11, 2,6-lutidine (64 μl, 550 μmol), dichloromethane (2 ml) and TBSOTf (84 μl, 366 mmol) to give the titled compound (47 mg, 91%) as a colorless oil.

$^1$H NMR : δ 0.04(3H, s), 0.06(3H, s), 0.07(3H, s), 0.08(3H, s), 0.85(9H, s), 0.88(9H, s), 1.10(3H, s), 1.19(3H, s), 2.04(3H, s), 3.18(1H, dd, J=7.4, 2.3 Hz), 5.15(1H, brs);

IR (neat) cm$^{-1}$: 2945, 1735:

MS(m/z): 553(M$^+$-Me), 173(100%).

Example 14

Synthesis of [3a(R)]-1(R)-[4(R),5-bis (t-butyldimethylsilyloxy)-1(S),5-dimethylhexyl]-4(S)-hydroxy-7a(R)-methyl-octahydro-1H-indene (compound 3a)

The [3a(R)]-4(S)-acetyloxy-1(R)-[4(R),5-bis (t-butyldimethylsilyloxy)-1(S),5-dimethylhexyl]-7a(R)-methyl-octahydro-1H-indene (compound 12a; 71 mg, 125 μmol) obtained in Example 12 was dissolved in THF (2 ml). The resulting solution was added dropwise to a suspension of lithium aluminum hydride (LiAlH$_4$) (20 mg, 528 μmol) in THF (1 ml) under cooling with ice, followed by stirring for 1.5 hours at the same temperature under argon atmosphere. Five droplets of 1N sodium hydroxide (NaOH) were added to the reaction mixture and then an aqueous Rochelle salt solution was added. The resulting mixture was extracted twice with ethyl acetate and washed with brine. The organic layer was dried over magnesium sulfate and distilled under reduced pressure to remove the solvent; the resulting residue was purified by flash column chromatography (12% ethyl acetate/hexane) to give the titled compound (63 mg, 96%) as a colorless oil.

$^1$H NMR: δ 0.03(3H, s), 0.06(3H, s), 0.07(3H, s), 0.08 (3H, s), 0.85(9H, s), 0.89(9H, s), 1.11(3H, s), 1.18(3H, s), 3.23(1H, brs), 4.08(1H, brs);

IR (neat) cm$^{-1}$: 3425(br), 2925;

MS(m/z): 511(M$^+$-Me), 173(100%).

Example 15

Synthesis of [3a(R)]-1(R)-[4(S),5-bis (t-butyldimethylsilyloxy)-1(S),5-dimethylhexyl]-4(S)-hydroxy-7a(R)-methyl-octahydro-1H-indene (Compound 3b)

The same procedure as in Example 14 was repeated using LiAlH$_4$ (6.3 mg, 166 μmol), THF (3 ml) and the [3a(R)]-4 (S)-acetyloxy-1-(R)-[4(S),5-bis(t-butyldimethylsilyloxy)-1 (S),5 -dimethylhexyl]-7a(R)-methyl-octahydro-1H-indene (compound 12b; 47 mg, 82.7 μmol) obtained in Example 13. The titled compound (44 mg, 100%) was obtained as a colorless oil.

$^1$H NMR: δ 0.04(3H, s), 0.067(3H, s), 0.072(3H, s), 0.08(3H, s), 0.85(9H, s), 0.89(9H, s), 0.92(3H, d, J=6.3 Hz), 1.11(3H, s), 1.19(3H, s), 3.18(1H, dd, J=7.6, 2.3 Hz), 4.00(1H, brs);

IR (neat) cm$^{-1}$: 3430(br), 2920;

MS(m/z): 511(M$^+$-Me), 173(100%).

The reactions performed in the above Examples 1 to 15 are shown below:

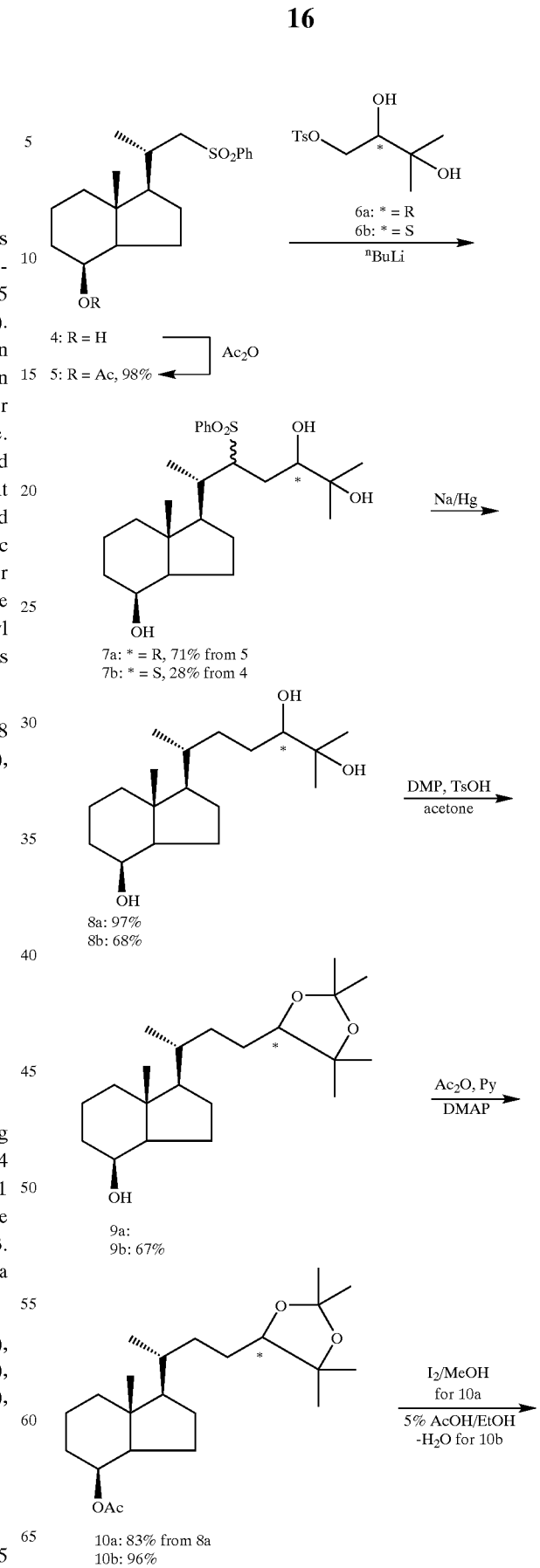

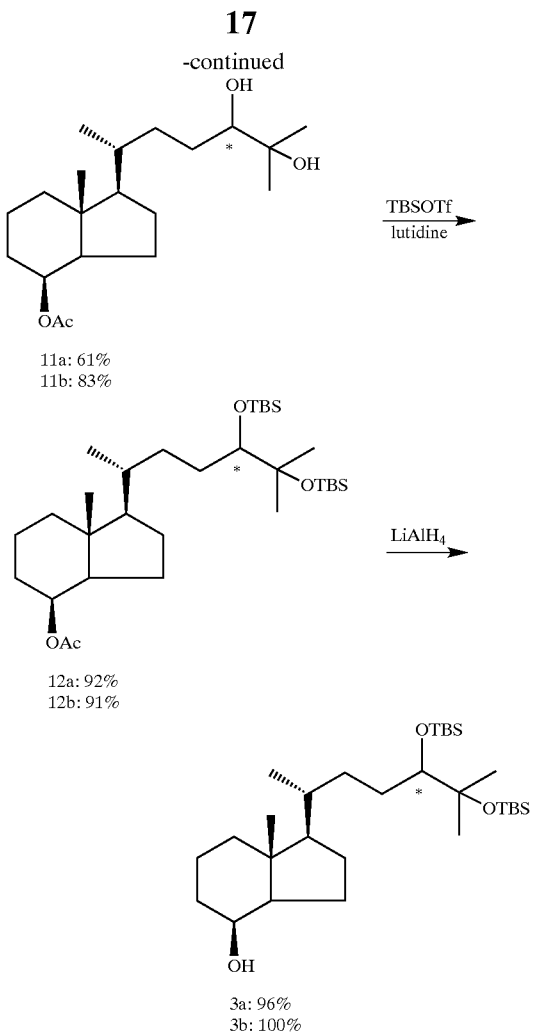

11a: 61%
11b: 83%

12a: 92%
12b: 91%

3a: 96%
3b: 100%

Example 16

Synthesis of [3a(R)]-1(R)-[4(R),5-bis (t-butyldimethylsilyloxy)-1(S),5-dimethylhexyl]-7a (R)-methyl-octahydro-1H inden-4-one (Compound 2a)

Tetra-n-propylammonium perruthenate (TPAP, 0.6 mg, 1.71 μmol) was added to a suspension in dichloromethane (1.3 ml) of the [3a(R)]-1(R)-[4(R),5-bis(t-butyldimethylsilyloxy)-1(S),5-dimethylhexyl]-4(S)-hydroxy-7a(R)-methyl-octahydro-1H-indene (compound 3a; 16.4 mg, 31.2 μmol) obtained in Example 14, 4-methylmorpholine N-oxide (NMO) (5.5 mg, 46.9 μmol) and molecular sieve 4A (6 mg), followed by stirring for 1 hour at room temperature under argon atmosphere. The reaction mixture was poured into a 10% $Na_2S_2O_3$ solution, extracted twice with dichloromethane and washed with brine. The organic layer was dried over magnesium sulfate and distilled under reduced pressure to remove the solvent; the resulting residue was purified by flash column chromatography (7% ethyl acetate/hexane) to give the titled compound (14 mg, 86%) as a colorless oil.

$^1$H NMR: δ 0.04(3H, s), 0.06(3H, s), 0.07(3H, s), 0.08 (3H, s), 0.63(3H, s), 0.85(9H, s), 0.89(9H, s), 0.95(3H, d, J=5.9 Hz), 1.11(3H, s), 1.19(3H, s), 2.45(1H, dd, J=11.5, 7.6 Hz), 3.23 (1H, brs);

IR(neat)cm$^{-1}$: 2950, 1715;

MS(m/z): 524(M$^+$), 173(100%).

Reference Example 1

Synthesis of 1(S),3(R),24(R),25 -tetrakis(t-butyldimethylsilyloxy)-9,10-secocholesta 5,7,10 (19)-triene (Compound 15a)

Under argon atmosphere at −80° C., n-butyllithium (1.47 mol/l,88 μl,129 μmol) was added dropwise to a solution in THF (0.5 ml) of 2-[3',5'-bis(t-butyldimethylsilyloxy)-2'-methylenecyclohexylidene]-1-diphenylphosphorylethane (compound 13, S. Hatakeyama et al., The Journal of Organic Chemistry, 54, 3515 (1989)) (45 mg, 77.3 μmol), followed by stirring at the same temperature for 5 min. A solution in THF (300 μl) of the [3a(R)]-1(R)-[4(R),5-bis (t-butyldimethylsilyloxy)-1(S),5-dimethylhexyl]-7a(R)-methyl-octahydro-1H-inden-4-one (compound 2a; 8.7 mg, 16.6 μmol) obtained in Example 16 was added dropwise to the resulting mixture, followed by stirring at the same temperature for 1 hour and then at room temperature for 10 min. The reaction mixture was poured into brine and extracted twice with ethyl acetate. The organic layer was dried over magnesium sulfate and distilled under reduced pressure to remove the solvent; the resulting residue was purified by preparative thin-layer chromatography (TLC) (3% ethyl acetate/hexane) to give the titled compound (7 mg, 48%) as a colorless oil.

$^1$H NMR: δ 0.04(3H, s), 0.06(3H, s), 0.07(15H, s), 0.08(3H, s), 0.53(3H, s), 0.86(9H, s), 0.877(9H, s), 0.881 (9H, s), 0.89(9H, s), 1.11(3H, s), 1.19(3H, s), 3.23(1H, brs), 4.15–4.23(1H, m), 4.36–4.41(1H, m), 4.87(1H, brd, J=2.6 Hz), 5.00(1H, s), 6.02(1H, d, J=11.1 Hz), 6.24(1H, d, J=11.1 Hz);

IR (neat) cm$^{-1}$: 2940; MS(m/z): 888(M$^+$), 173(100%);

UV λ max nm: 264, min nm: 227.

Reference Example 2

Synthesis of 1(S),3(R),24(R),25 -tetrahydroxy-9,10-secocholesta-5,7,10(19)-triene (Compound 14a)

The 1(S),3(R),24(R),25-tetrakis (t-butyldimethylsilyloxy)-9,10-secocholesta-5,7,10(19)-triene (compound 15a; 7 mg, 7.88 μmol) obtained in Reference Example 1 was dissolved in 1,3-dimethyl-2-imidazolidinone (DMI) (3 ml). To the resulting solution, tetra-n-butylammonium fluoride (TBAF) (1 mol/l, 300 μl, 300 μmol) was added, followed by stirring for 2 hours under argon atmosphere at 105° C. The reaction mixture was poured into water, extracted twice with ethyl acetate and washed twice with water. The organic layer was dried over magnesium sulfate and distilled under reduced pressure to remove the solvent; the resulting residue was purified by preparative thin-layer chromatography (TLC) (ethanol:hexane=3:25) to give the titled compound (2.7 mg, 79%) as a white powder.

$^1$H NMR: δ 0.55(3H, s), 0.94(3H, d, J=5,9 Hz), 1.17(3H, s), 1.22(3H, s), 2.31(1H, dd, J=13.2, 6.6 Hz), 2.60(1H, dd, J=13.5, 3.6 Hz), 2.82(1H, dd, J=10.6, 3.6 Hz), 3.31–3.37 (1H, m), 4.18–4.27(1H, m), 4.40–4.48(1H, m), 5.00(1H, s), 5.33(1H, s), 6.02(1H, d, J=11.4 Hz), 6.38(1H, d, J=11.4 Hz);

IR (KBr) cm$^{-1}$: 3380(br), 2925;

MS(m/z): 432(M$^+$), 134(100%);

UV λ max nm:264,min nm:227.

The reactions involved in the above Example 16 and Reference Examples 1 and 2 are shown below:

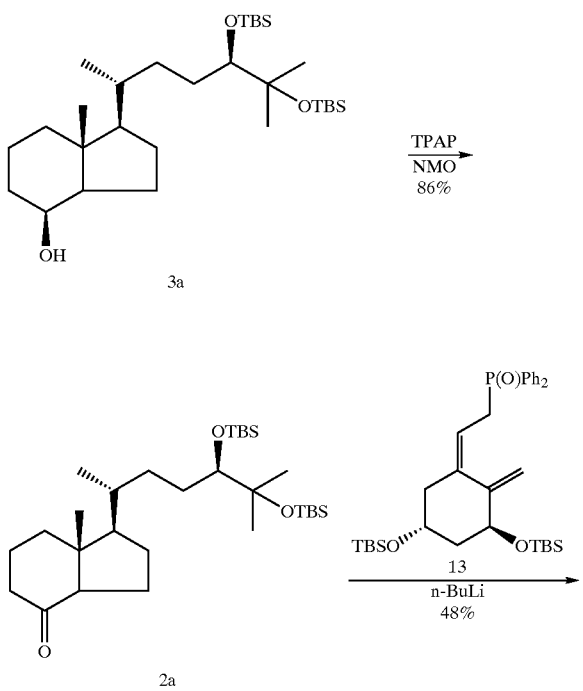

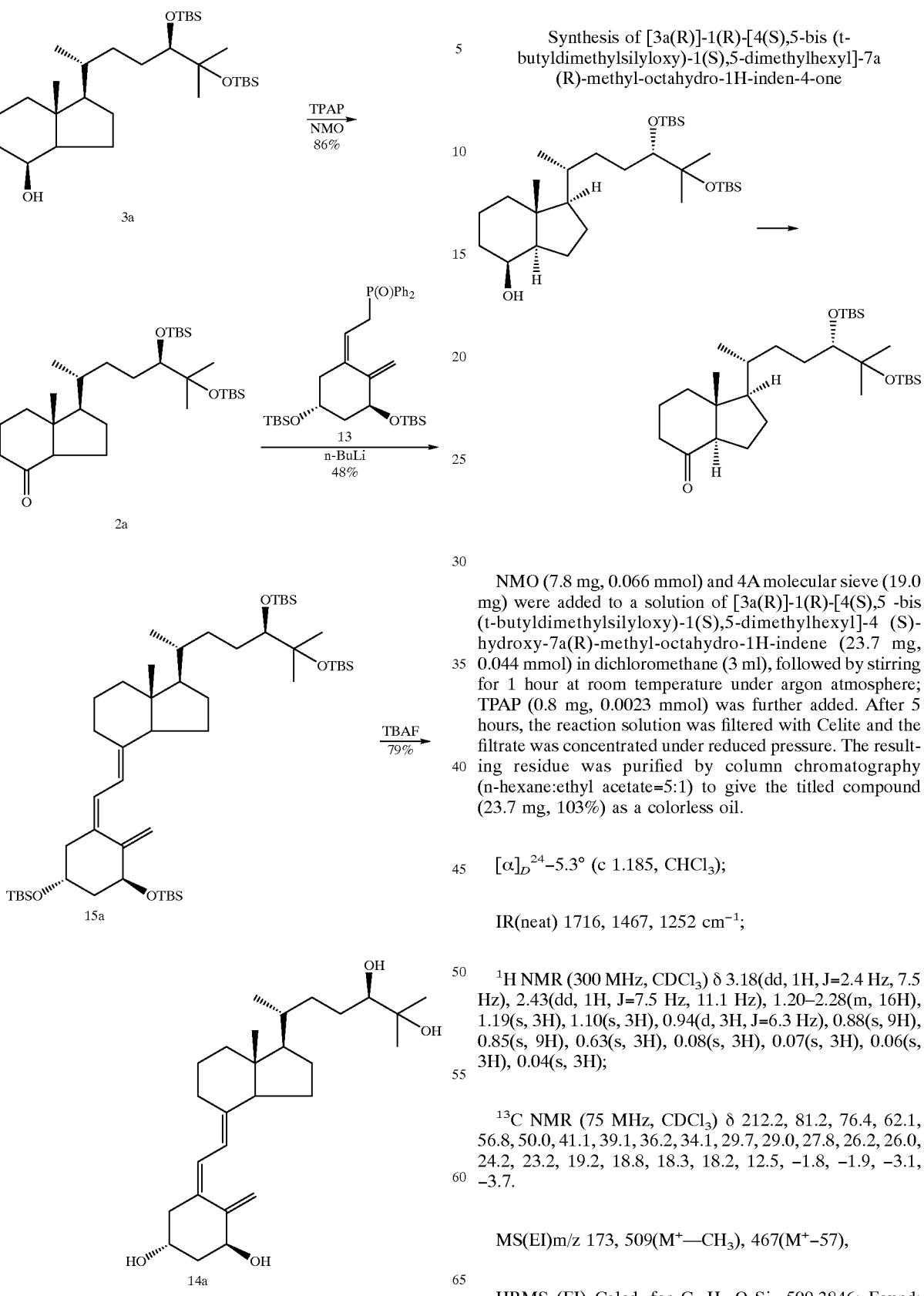

Example 17

Synthesis of [3a(R)]-1(R)-[4(S),5-bis (t-butyldimethylsilyloxy)-1(S),5-dimethylhexyl]-7a(R)-methyl-octahydro-1H-inden-4-one NMO (7.8 mg, 0.066 mmol) and 4A molecular sieve (19.0 mg) were added to a solution of [3a(R)]-1(R)-[4(S),5 -bis (t-butyldimethylsilyloxy)-1(S),5-dimethylhexyl]-4 (S)-hydroxy-7a(R)-methyl-octahydro-1H-indene (23.7 mg, 0.044 mmol) in dichloromethane (3 ml), followed by stirring for 1 hour at room temperature under argon atmosphere; TPAP (0.8 mg, 0.0023 mmol) was further added. After 5 hours, the reaction solution was filtered with Celite and the filtrate was concentrated under reduced pressure. The resulting residue was purified by column chromatography (n-hexane:ethyl acetate=5:1) to give the titled compound (23.7 mg, 103%) as a colorless oil.

$[\alpha]_D^{24}$ -5.3° (c 1.185, CHCl$_3$);

IR(neat) 1716, 1467, 1252 cm$^{-1}$;

$^1$H NMR (300 MHz, CDCl$_3$) δ 3.18(dd, 1H, J=2.4 Hz, 7.5 Hz), 2.43(dd, 1H, J=7.5 Hz, 11.1 Hz), 1.20–2.28(m, 16H), 1.19(s, 3H), 1.10(s, 3H), 0.94(d, 3H, J=6.3 Hz), 0.88(s, 9H), 0.85(s, 9H), 0.63(s, 3H), 0.08(s, 3H), 0.07(s, 3H), 0.06(s, 3H), 0.04(s, 3H);

$^{13}$C NMR (75 MHz, CDCl$_3$) δ 212.2, 81.2, 76.4, 62.1, 56.8, 50.0, 41.1, 39.1, 36.2, 34.1, 29.7, 29.0, 27.8, 26.2, 26.0, 24.2, 23.2, 19.2, 18.8, 18.3, 18.2, 12.5, −1.8, −1.9, −3.1, −3.7.

MS(EI)m/z 173, 509(M$^+$—CH$_3$), 467(M$^+$−57),

HRMS (EI) Calcd. for C$_{29}$H$_{57}$O$_3$Si$_2$ 509.3846; Found: 509.3852.

Example 18

Synthesis of [3a(R)]-1(R)-[4(R),5-bis (t-butyldimethylsilyloxy)-1(S),5-dimethylhexyl]-7a(R)-methyl-octahydro-1H-inden-4-one

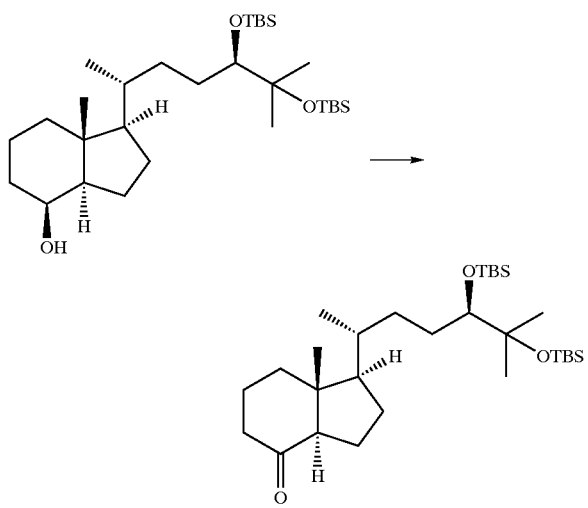

NMO (7.0 mg, 0.059 mmol) and 4A molecular sieve (14.0 mg) were added to a solution of [3a(R)]-1(R)-[4(R),5 -bis (t-butyldime-thylsilyloxy)-1(S),5-dimethylhexyl]-4 (S)-hydroxy-7a(R)-methyl-octahydro-1H-indene (15.4 mg, 0.029 mmol) in dichloromethane (2 ml), followed by stirring for 1 hour at room temperature under argon atmosphere; TPAP (0.8 mg, 0.0023 mmol) was further added. After 2.5 hours, the reaction solution was filtered with Celite and the filtrate was concentrated under reduced pressure. The resulting residue was purified by column chromatography (n-hexane:ethyl acetate=5:1) to give the titled compound (14.8 mg, 96%) as a colorless oil.

$[\alpha]_D^{23}$ +17° (c 0.83, CHCl$_3$);

IR (neat) 1716, 1460, 1252 cm$^{-1}$;

$^1$H NMR (300MHz, CDCl$_3$) δ 3.18–3.24 (m, 1H), 2.45 (dd, 1H, J=7.5 Hz, 11.1 Hz), 1.20–2.34(m, 16H), 1.18(s, 3H), 1.11(s, 3H), 0.94(d, 3H, J=5.7 Hz), 0.89(s, 9H), 0.85(s, 9H), 0.63(s, 3H), 0.08(s, 3H), 0.07(s, 3H), 0.06(s, 3H), 0.04(s, 3H);

$^{13}$C NMR (75 MHz, CDCl$_3$) δ 212.2, 81.0, 76.4, 62.1, 56.7, 50.0, 41.1, 39.1, 36.3, 33.8, 29.6, 29.0, 27.6, 26.2, 25.9, 24.2, 23.6, 19.2, 18.9, 18.3, 18.2, 12.6, −1.8, −1.9, −3.1, −3.9.

MS (EI) m/z 173, 509 (M$^+$—CH$_3$), 467 (M+−57),

HRMS(EI) Calcd. for C$_{29}$H$_{57}$O$_3$Si$_2$ 509.3846; Found 509.3845.

Example 19

Synthesis of [3a(R)]-1(R)-[4(S),5-bis (t-butyldimethylsilyloxy)-1(S),5-dimethylhexyl]-4 (E)-bromomethylene-7a(R)-methyl-octahydro-1H-indene

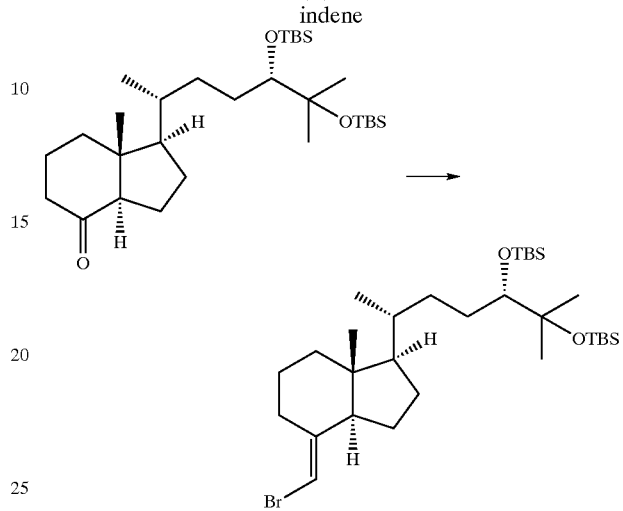

To a solution of (bromomethylene)triphenylphosphonium bromide (159.3 mg, 0.37 mmol) in THF (0.9 ml), sodium bis(trimethylsilyl)amide (in THF at 1M, 355 μl, 0.36 mmol) was added at −60° C., followed by stirring for 1 hour under argon atmosphere. Immediately after adding a solution in THF (0.3 ml) of the [3a(R)]-1(R)-[4(S),5-bis (t-butyldimethylsilyloxy)-1(S),5-dimethylhexyl]-7a(R)-methyl-octahydro-1H-inden-4-one (23.9 mg, 0.046 mmol) obtained in Example 17, the reaction temperature was returned to room temperature. After 1 hour, the resulting mixture was diluted with n-hexane and filtered with silica gel; the filtrate was concentrated under reduced pressure. The resulting residue was purified by preparative TLC (n-hexane) to give the titled compound (15.6 mg, 57%) as a yellow oil.

$[\alpha a]_D^{23}$ +47.31° (c 0.78, CHCl$_3$);

IR (neat) 1466, 1252 cm$^{-1}$;

$^1$H NMR (300 MHz, CDCl$_3$) δ 5.64(s, 1H), 3.18(dd, 1H, J=2.1 Hz, 7.5 Hz), 2.82–2.91(m, 1H), 1.00–2.16(m, 16H), 1.19(s, 3H), 1.10(s, 3H), 0.92(d, 3H, J=6.0 Hz), 0.88(s, 9H), 0.85(s, 9H), 0.56(s, 3H), 0.08(s, 3H), 0.07(s, 3H), 0.06(s, 3H), 0.04(s, 3H);

$^{13}$C NMR (75 MHz, CDCl$_3$) δ 145.3, 97.4, 81.2, 76.4, 56.0, 55.9, 45.6, 40.0, 36.7, 34.2, 31.2, 29.7, 29.0, 27.9, 26.2, 25.9, 23.2, 22.7, 22.1, 18.9, 18.3, 18.2, 11.9, −1.8, −1.9, −3.1, −3.7.

MS(EI)m/z 73, 585 (M$^+$—CH$_3$), 543 (M$^+$−57),

HRMS(EI) Calcd. for C$_{27}$H$_{52}$O$_2$Si$_2$Br 543.2689; Found 543.2692.

Example 20

Synthesis of [3a(R)]-1(R)-[4(R),5-bis(t-butyldimethylsilyloxy)-1(S),5-dimethylhexyl]-4(E)-bromomethylene-7a(R)-methyl-octahydro-1H-indene

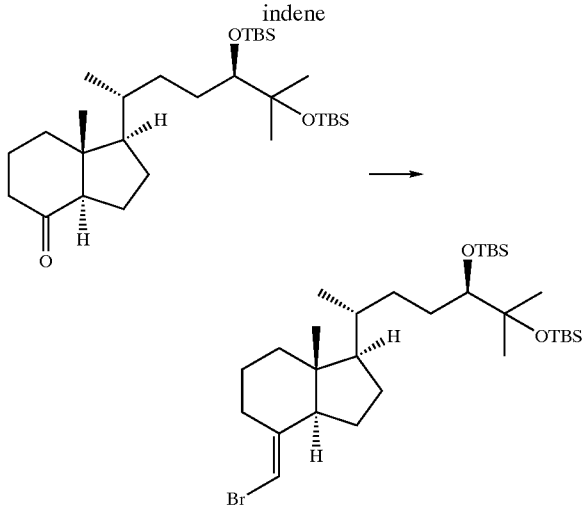

To a solution of (bromomethylene)triphenylphosphonium bromide (130.5 mg, 0.30 mmol) in THF (1.0 ml), sodium bis(trimethylsilyl)amide (in THF at 1M, 290 μl, 0.29 mmol) was added at −60° C., followed by stirring for 1 hour under argon atmosphere. Immediately after adding a solution in THF (0.3 ml) of the [3a(R)]-1(R)-[4(R),5-bis(t-butyldimethylsilyloxy)-1(S),5-dimethylhexyl]-7a(R)-methyl-octahydro-1H-inden-4-one (19.6 mg, 0.037 mmol) obtained in Example 18 the reaction temperature was returned to room temperature. After 1 hour, the resulting mixture was diluted with n-hexane and filtered with silica gel; the filtrate was concentrated under reduced pressure. The resulting residue was purified by preparative TLC (n-hexane) to give the titled compound (11.0 mg, 49%) as a yellow oil.

$[\alpha]_D^{21}$ −106.18° (c 0.55, CHCl$_3$);

IR (neat) 1467, 1253cm$^{-1}$;

$^1$H NMR (300 MHz, CDCl$_3$) δ 5.64(s, 1H), 3.18–3.24(m, 1H), 2.82–2.91(m, 1H), 1.20–2.04(m, 16H), 1.18(s, 3H), 1.11(s, 3H), 0.92(d, 3H, J=6.0 Hz), 0.89(s, 9H), 0.85(s, 9H), 0.56(s, 3H), 0.08(s, 3H), 0.07(s, 3H), 0.06(s, 3H), 0.04(s, 3H);

$^{13}$C NMR (75 MHz, CDCl$_3$) δ 145.3, 97.4, 81.1, 76.4, 56.0, 55.9, 45.6, 40.0, 36.8, 33.9, 31.2, 29.6, 29.1, 27.7, 26.2, 26.0, 23.6, 22.7, 22.2, 19.0, 18.3, 18.2, −1.8, −1.9, −3.1, −3.9.

MS (EI) m/z 73, 585 (M$^+$−CH$_3$), 543 (M$^+$−57),

HRMS(EI) Calcd. for C$_{30}$H$_{58}$O$_2$Si$_2$Br 585.3150; Found for C$_{30}$H$_{58}$O$_2$Si$_2$Br 585.3134.

Example 21

Synthesis of 3,5-bis(t-butyldimethylsilyloxy)-4-(3-t-butyldimethylsilyloxypropoxy)-1-octen-7-ine

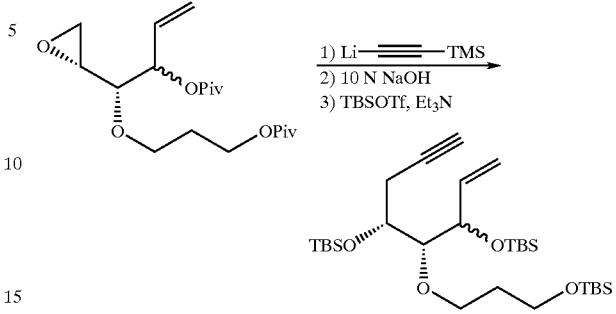

A 1.59M solution of n-butyllithium in n-hexane (35.2 ml, 56.0 mmol) was added to a solution of trimethylsilylacetylene (8.4 ml, 11.9 mmol) in THF (30 ml) at −78° C., followed by stirring for 30 min.; boron trifluoride diethyl ether (11.9 mmol) was further added and the mixture was stirred for 1 hour. To the resulting mixture, a solution of a 1:1 mixture of (4R)- and (4S)-epimers of 1,2-epoxy-4-pivaloyloxy-3-(3'-pivaloyloxypropoxy)-5-hexene (4.24 g, 11.9 mmol) in THF (65 ml) was added dropwise at −78° C., followed by stirring for 2 hours. A saturated aqueous solution of NaHCO$_3$ was added to the resulting reaction solution, extracted with ethyl acetate, washed with brine, dried (MgSO$_4$) and then distilled under reduced pressure to remove the solvent, giving a yellow oil (5.1 g).

Methanol (80 ml) and 10 N aqueous sodium hydroxide (35 ml) were added to the above yellow oil (5.1 g), followed by stirring for one hour and a half at room temperature. The resulting mixture was neutralized with concentrated hydrochloric acid under cooling with ice, azeotropically distilled with toluene to remove water and extracted with THF. The extract was dried (MgSO$_4$) and then distilled under reduced pressure to remove the solvent; the resulting residue was purified on a short column (ethyl acetate) to give a triol compound, 3,5-dihydroxy-4-(3-hydroxypropoxy)-1-octen-7-ine (1.73 g).

The above triol compound (1.73 g) was dissolved in dichloromethane (100 ml) and mixed with triethylamine (11.3 ml, 0.4 mol) and TBSOTf (10.7 ml, 40.4 mmol) at 0° C. The mixture was stirred for one hour and a half at 0° C. mixed with a saturated aqueous NaHCO$_3$ solution and extracted with dichloromethane. The extract was washed with brine, dried (MgSO$_4$) and distilled under reduced pressure to remove the solvent. The resulting residue was purified by flash column chromatography (n-hexane: ethyl acetate=50:1) to give Fraction 1 (epimer mixture=1.1265 g), Fraction 2 (epimer mixture=2.4804 g) and Fraction 3 (S form=334.8 mg) (yield of the epimer mixtures=3.9417 g, 60% from the epoxied). Fraction 1 was further separated by flash column chromatography (n-hexane: ethyl acetate=50:1) to give an R form (169.3 mg) and an epimer mixture (789.4 mg).

R form $[\alpha]_D^{25}$ +15.4° (c 0.52, CHCl$_3$);

IR (neat) 3314, 1468, 1254cm$^{-1}$;

$^1$H NMR (300 MHz, CDCl$_3$) δ 5.89(ddd, 1H, J=6.0 Hz, 10.5 Hz, 17.4 Hz), 5.26(dt, 1H, J=1.5 Hz, 17.1 Hz), 5.14(dt, 1H, J=1.5 Hz, 10.5 Hz), 4.18(t, 1H, J=6.3 Hz), 3.98(ddd, 1H, J=1.8 Hz, 4.8 Hz, 7.2 Hz), 3.60–3.82(m, 4H), 3.27(dd, 1H, J=2.1 Hz, 6.6 Hz), 2.46(ddd, 1H, J=3.0 Hz, 5.1 Hz, 17.1 Hz), 1.92(t, 1H, 2.7 Hz), 1.78(quint, 2H, J=6.0 Hz), 0.89–0.90(m, 2H), 0.10(s, 3H), 0.08(s, 3H), 0.06(s, 3H), 0.04(s, 6H), 0.03(s, 3H);

$^{13}$C NMR(75 MHz, CDCl$_3$) δ 138.5, 116.0, 86.9, 83.2, 74.4, 72.1, 69.5, 60.5, 33.7, 26.1, 26.0, 23.3, 18.5, 18.4, −4.3, −4.4, −4.5, −5.2.

MS(EI)m/z 147(100%), 556, 541, 499.

HRMS (EI) Calcd. for C$_{28}$H$_{57}$O$_4$Si$_3$ 541.3565; Found for C$_{28}$H$_{57}$O$_4$Si$_3$ 541.3547.

S form $[α]_D^{25}$ −2.3° (c.0.80, CHCl$_3$);

IR(neat) 3314, 1468, 1254 cm$^{-1}$;

$^1$H NMR (300 MHz, CDCl$_3$) δ 5.88(ddd, 1H, J=6.0 Hz, 10.2 Hz, 17.4 Hz), 5.26(dt, 1H, J=1.5 Hz, 17.1 Hz), 5.14(dt, 1H, J=1.5 Hz, 10.5 Hz), 4.27(dd, 1H, J=4.5 Hz, 6.0 Hz), 3.85(dt, 1H, J=4.2 Hz, 5.7 Hz), 3.74(ddd, 2H, J=3.0 Hz, 6.3 Hz, 12.9 Hz), 3.67(t, 2H, J=6.3 Hz), 3.36(dd, 1H, J=4.5 Hz, 5.7 Hz), 2.53(ddd, 1H, J=2.7 Hz, 5.7 Hz, 17.4 Hz), 1.93(t, 1H, J=2.7 Hz), 1.74(quint, 2H, J=6.3 Hz), 0.91(s, 9H), 0.90(s, 9H), 0.88(s, 9H), 0.03–0.12(m, 18H);

$^{13}$C NMR (75 MHz, CDCl$_3$) δ 138.2, 116.1, 85.7, 82.3, 74.4, 71.0, 69.8, 69.7, 60.3, 33.7, 26.1, 26.0, 23.3, 18.5, 18.2, 18.2, −4.2, −4.3, −4.4, −4.7, −5.2.

Example 22

Synthesis of (5Z,7E)-(1R,2R,3R,24S)-1,3,24,25-tetrakis(t-butyldimethylsilyloxy)-2-(3-t-butyldimethylsilyl-oxypropoxy)-9,10-secocholesta-5,7,10(19)-triene

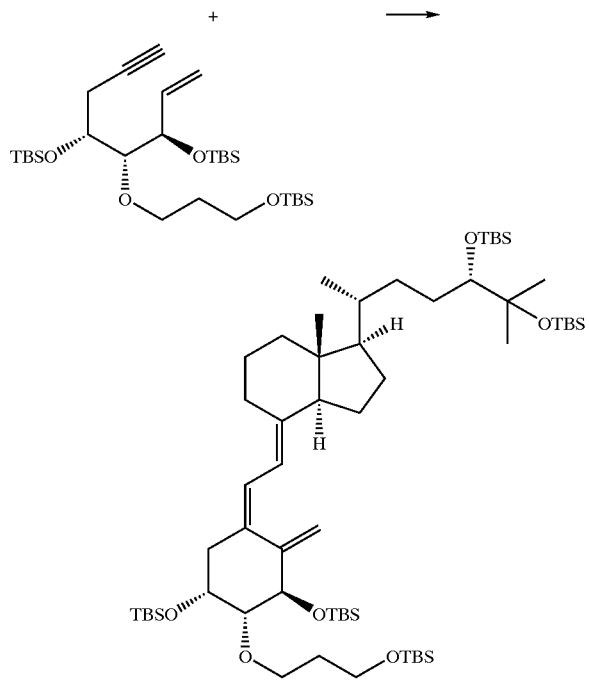

A mixture solution of triphenylphosphine (2.4 mg, 0.0092 mmol) and tris(dibenzylidene-acetone) (chloroform) dipalladium(0) (1.7 mg, 0.0016 mmol) in toluene (0.2 ml) and triethylamine (0.3 ml) was stirred at room temperature for 10 min. and then mixed with a mixture solution in toluene (0.2 ml) of the [3a(R)]-1(R)-[4(S),5-bis(t-butyldimethylsilyloxy)-1(S),5-dimethylhexyl]-4 (E)-bromomethylene-7a(R)-methyl-octahydro-1H-indene (15.6 mg, 0.026 mmol) obtained in Example 19 and the 3(R)-3,5-bis (t-butyldimethylsilyloxy)-4-(3-t-butyldimethylsilyloxypropoxy)-1-octen-7-ine (9.6 mg, 0.017 mmol) obtained in Example 21, followed by heating under reflux for 4 hours. The resultant was diluted with n-hexane, filtered with silica gel and concentrated under reduced pressure. The resulting residue was purified by preparative TLC (n-hexane:benzene=2:1) to give the titled compound (6.2 mg, 34%) as a colorless oil.

$[α]_D^{23}$ +10.7° (c0.31, CHCl$_3$); IR (neat) 1467, 1252 cm$^{-1}$;

$^1$H NMR (300 MHz, CDCl$_3$) δ 6.22(d, 1H, J=10.5 Hz), 6.00(d, 1H, J=10.8 Hz), 5.26(br s, 1H), 4.98(br s, 1H), 4.16–4.26(m, 2H), 3.58–3.76(m, 4H), 3.16–3.24(m, 2H), 2.81(br d, 1H, J=13.5 Hz), 2.46(br dd, 1H, J=11.6 Hz, 8.1 Hz), 2.22(br dd, 1H, J=12.6 Hz, 3.8 Hz), 1.20–2.05(m, 18H), 1.19(s, 3H), 1.11(s, 3H), 0.82–0.94(m, 48H), 0.52(s, 3H), 0.02–0.10(m, 30H).

Example 23

Synthesis of (5Z,7E)-(1R,2R,3R,24R)-1,3,24,25-tetrakis(t-butyldimethylsilyloxy)-2-(3-t-butyldimethyl-silyloxypropoxy)-9,10-secocholesta-5,7,10(19)-triene

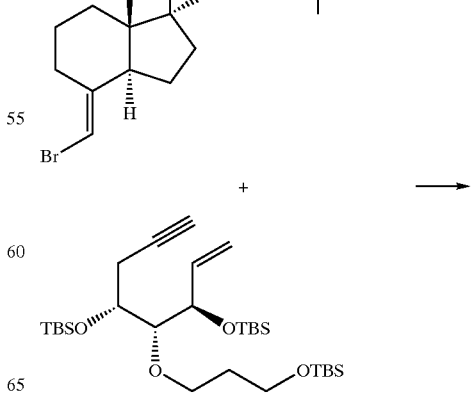

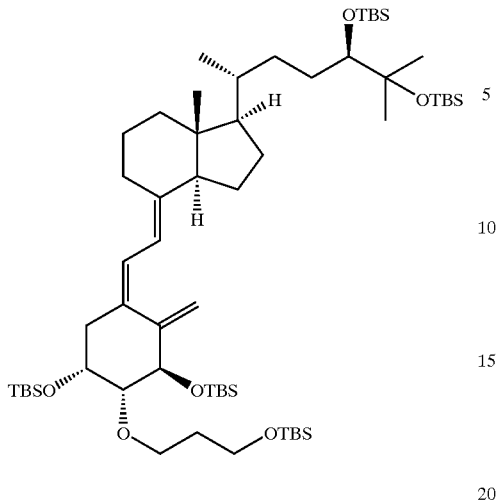

The same procedure as in Example 22 was repeated by replacing the [3a(R)]-1(R)-[4(S),5-bis(t-butyldimethylsilyloxy)-1(S),5-dimethylhexyl]-4 (E)-bromomethylene-7a(R)-methyl-octahydro-1H-indene with the [3a(R)]-1(R)-[4(R),5-bis(t-butyldimethylsilyloxy)-1(S),5 -dimethylhexyl]-4(E)-bromomethylene-7a(R)-methyl-octahydro-1H-indene obtained in Example 20. The titled compound (6.3 mg 36%) was obtained as a colorless oil.

$[\alpha]_D^{23}$ +25.8° (c 0.28, CHCl$_3$);

IR (neat) 1467, 1252 cm$^{-1}$;

$^1$H NMR (300 MHz, CDCl$_3$) δ 6.22(d, 1H, J=10.5 Hz), 6.00(d, 1H, J=10.8 Hz), 5.26(br s, 1H), 4.98(br s, 1H), 4.16–4.26(m, 2H), 3.58–3.76(m, 4H), 3.22(m, 2H), 2.81(br d, 1H, J=12.3 Hz), 2.46(br dd, 1H, J=12.9 Hz, 7.8 Hz), 2.23(br dd, 1H, J=12.6 Hz, 3.3 Hz), 1.20–2.05(m, 18H), 1.18(s, 3H), 1.11(s, 3H), 0.82–0.94(m, 48H), 0.52(s, 3H), 0.02–0.10(m, 30H).

Example 24

Synthesis of (5Z,7E)-(1R,2R,3R,24S)-2-(3-hydroxypropoxy)-9,10-secocholesta-5,7,10(19)-triene-1,3,24,25-tetraol Under argon atmosphere, a 1M-TBAF-THF solution (237 μl, 237 μmol) was added to a solution of (5Z,7E)-(1R,2R,3R,24S)-1,3,24,25-tetrakis(t-butyldimethylsilyloxy)-2-(3-t-butyldimethylsilyloxypropoxy)-9,10-secocholesta-5,7,10(19)-triene (compound 20a; 5.1 mg, 4.73 μmol) in toluene (0.5 ml), followed by stirring for 2 hours under heating at an external temperature of 105° C. After cooling to room temperature, the reaction solution was diluted with ethyl acetate, washed twice with water and once with brine, dried over anhydrous magnesium sulfate and distilled under reduced pressure to remove the solvent. The resulting residue was purified by preparative TLC (the thickness of silica gel: 0.25 mm, dichloromethane;ethanol=5:1) to give the titled compound (compound 1a; 1.45 mg, 60%) as a colorless oil.

$[\alpha]_D^{24}$ −49° (c0.07, EtOH);

$^1$H NMR(270 MHz, CDCl$_3$) δ 0.55(s, 3H), 0.95(d, J=6.3 Hz, 3H), 1.16(s, 3H), 1.22(s, 3H), 2.42(brd, J=13.9 Hz, 1H), 2.55(dd, J=14.5, 4.0 Hz, 1H), 2.75–2.87(m, 1H), 3.20–3.37 (m, 2H), 3.68–3.78(m, 1H), 3.80–3.99(m, 3H), 4.20–4.36 (m, 2H), 5.08(brs, 1H), 5.50(brs, 1H), 6.04(d, J=11.2 Hz, 1H), 6.36(d, J=11.2 Hz, 1H);

IR(neat,cm$^{-1}$) 3400, 2947, 2929, 2873, 1378, 1107, 1072;

UV(EtOH) λ max 264 nm.

Example 25

Synthesis of (5Z,7E)-(1R,2R,3R,24R)-2-(3-hydroxypropoxy)-9,10-secocholesta-5,7,10(19)-triene-1,3,24,25-tetraol The same procedure as in Example 24 was repeated using (5Z,7E)-(1R,2R,3R,24R)-1,3,24,25-tetrakis(t-butyldimethylsilyloxy)-2-(3-t-butyldimethylsilyloxypropoxy)-9,10-secocholesta-5,7,10(19)-triene (compound 20b; 3.3 mg, 3.06 μmol), toluene (0.5 ml), a 1M-TBAF-THF solution (153 μl, 237 μmol) to give the titled compound (compound 1b; 1.02 mg, 66%) as a colorless oil.

$[\alpha]_D^{24}$ −23° (c0.07, EtOH);

$^1$H NMR (270 MHz, CDCl$_3$) δ 0.56(s, 3H), 0.94(d, J=5.9 Hz, 3H), 1.16(s, 3H), 1.22(s, 3H), 2.42(brd, J=14.5 Hz, 1H), 2.55(dd, J=14.5, 4.0 Hz, 1H), 2.76–2.87(m, 1H), 3.27(dd, J=8.8, 2.8 Hz, 1H), 3.30–3.37(m, 1H), 3.68–3.78(m, 1H), 3.80–4.00(m, 3H), 4.21–4.36(m, 2H), 5.08(brs, 1H), 5.50 (brs, 1H), 6.04(d, J=11.2 Hz, 1H), 6.36(d, J=11.2 Hz, 1H);

IR(neat, cm$^{-1}$) 3400, 2947, 2927, 2871, 1377, 1105, 1070;

UV(EtOH)λ max 264 nm.

The reactions involved in the above Examples 24 and 25 are shown below.

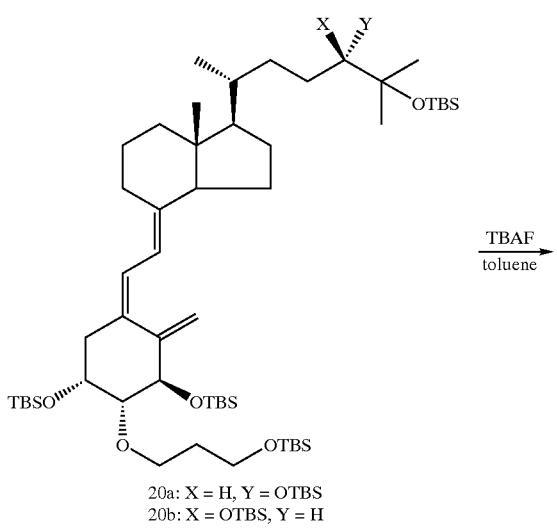

20a: X = H, Y = OTBS
20b: X = OTBS, Y = H

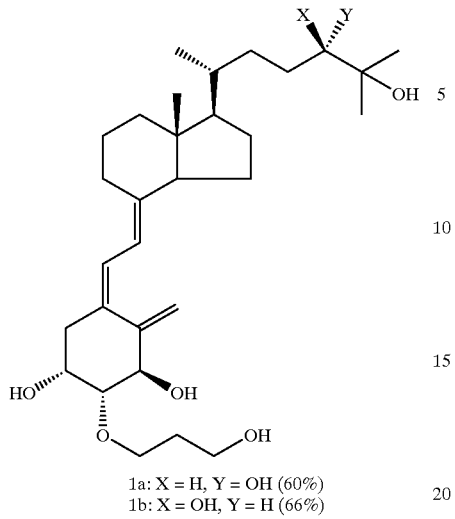

1a: X = H, Y = OH (60%)
1b: X = OH, Y = H (66%)

Reference Example 3

Synthesis of [3a(R)]-4(S)-acetyloxy-1(R)-[1(S),5-dimethyl-5-triethylsilyloxyhexyl]-7a(R)-methyl-octahydro-1H-indene (Compound 2)

Triethylsilyl trifluoromethanesulfonate (TESOTf) (1.3 ml, 5.53 mmol) was added to a solution of [3a(R)]-4(S)-acetyloxy-1(R)-[1(S),5-dimethyl-5-hydroxyhexyl]-7a(R)-methyl-octahydro-1H-indene (compound 1, Hatakeyama, S. et al. disclosed in The Journal of Organic Chemistry, 56, 461 (1991), 1.38 g, 4.25 mmol) and 2,6-lutidine (0.79 ml, 6.80 mmol) in dichloromethane (10 ml), followed by stirring for 30 min. The reaction solution was diluted with dichloromethane, washed with ice-cooled 0.5N hydrochloric acid and saturated aqueous sodium hydrogencarbonate and dried over magnesium sulfate. The dried product was distilled under reduced pressure to remove the solvent and purified by silica gel column chromatography (hexane:ethyl acetate=19:1) to give the titled compound (1.66 g, 89%) as a colorless oil.

$^1$H NMR (200 MHz, CDCl$_3$), δ 0.49–0.63(m, 6H), 0.87–1.01(m, 15H), 1.18(s, 6H), 2.04(s, 3H), 5.14(br, 1H).

Reference Example 4

Synthesis of [3a(R)]-1(R)-[1(S),5 -dimethyl-5-triethylsilyloxyhexyl]-4(S)-hydroxy-7a(R)-methyl-octahydro-1H-indene (Compound 3)

A portion of [3a(R)]-4(S)-acetyloxy-1(R)-[1(S),5-dimethyl-5-triethylsilyloxyhexyl]-7a(R)-methyl-octahydro-1H-indene (compound 2, 1.65 g, 3.76 mmol) obtained in Reference Example 3 was dissolved in THF (15 ml). The solution was cooled to 0° C. and then slowly mixed with LiAlH$_4$ (214 mg, 5.64 mmol), followed by stirring for 30 min. at room temperature. After treating the excess LiAlH$_4$ with ethyl acetate, the mixture was poured into a 10% aqueous NaOH solution and extracted twice with ethyl acetate. The extract was washed with brine, dried over anhydrous magnesium sulfate and then distilled under reduced pressure to remove the solvent. The resulting residue was purified by silica gel column chromatography (n-hexane: ethyl acetate=10:1) to give the titled compound (1.57 g, quantitatively) as a colorless oil.

$^1$H NMR (200 MHz, CDCl$_3$), δ 0.49–0.63(m, 6H), 0.86–1.01(m, 15H), 1.18(s, 6H), 4.07(br, 1H).

The reactions involved in the above Reference Examples 3 and 4 are shown below.

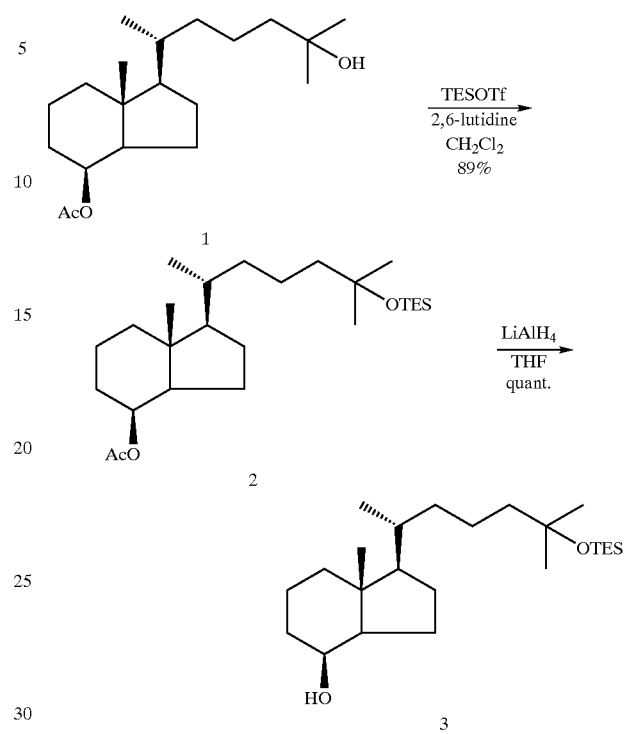

Reference Example 5

Synthesis of [3a(R)]-1(R)-[1(S),5 -dimethyl-5-triethylsilyloxyhexyl]-7a(R)-methyl-4-oxo-octahydro-1H-indene

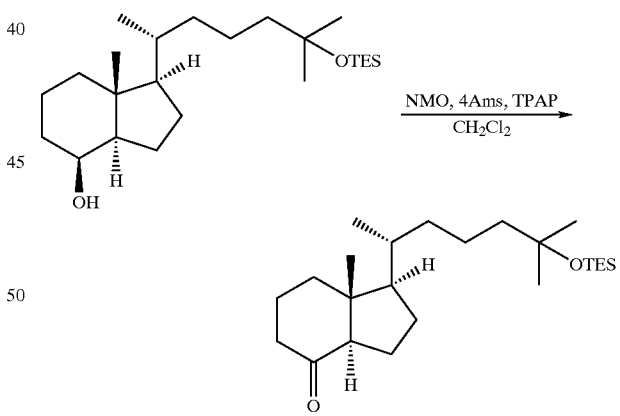

NMO (4.1 mg, 0.035 mmol) and 4A molecular sieve (12.9 mg) were added to a solution in dichloromethane (3 ml) of the [3a(R)]-1(R)-[1(S),5-dimethyl-5-triethylsilyloxyhexyl]-4 (S)-hydroxy-7a(R)-methyl-octahydro-1H-indene (10.3 mg, 0.026 mmol) obtained in Reference Example 4, followed by stirring for 1 hour at room temperature under argon atmosphere. TPAP (0.5 mg, 0.0014 mmol) was further added to the mixture. After 6.5 hours, the reaction solution was filtered with Celite and the filtrate was concentrated under reduced pressure. The resulting residue was purified by column chromatography (n-hexane:ethyl acetate=5:1) to give the titled compound (10.0 mg, 97%) as a colorless oil.

$^1$H NMR (300 MHz, CDCl$_3$) δ 2.45(dd, 1H, J=9.0 Hz, 12.5 Hz), 1.21–2.35(m, 18H), 1.19(s, 6H), 0.94(s, 3H), 0.94(t, 9H, J=8.0 Hz), 0.65(s, 3H), 0.56(q, 6H, J=8.0 Hz).

Reference Example 6

Synthesis of [3a(R)]-4 (E)-bromomethylene-1(R)-[1(S),5-dimethyl-5 -triethylsilyloxyhexyl]-7a(R)-methyl-octahydro-1H-indene

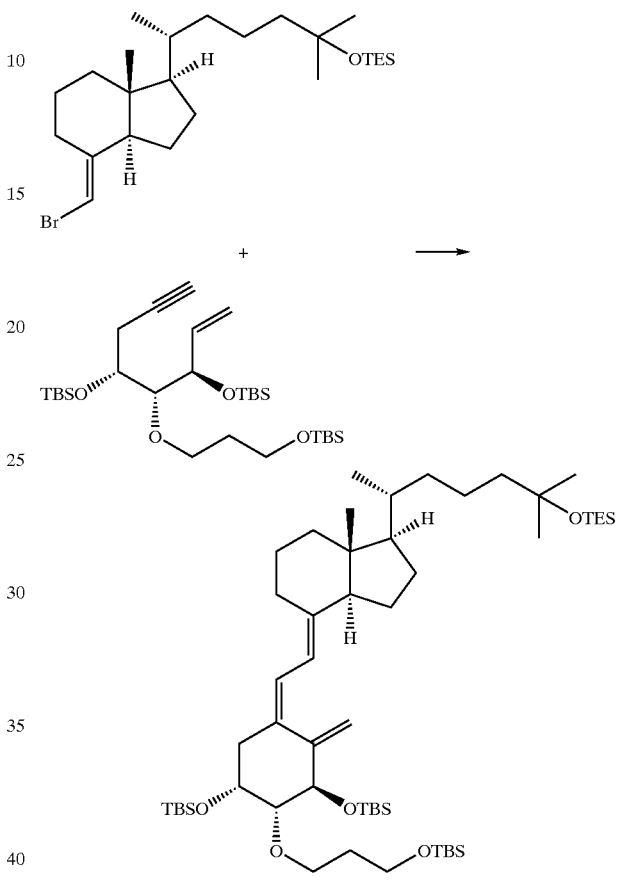

Sodium bis(trimethylsilyl)amide (in THF at 1M, 455 μl, 0.46 mmol) was added to a solution of (bromomethylene)triphenylphosphonium bromide (205 mg, 0.47 mmol) in THF (1.1 ml) at −60° C., followed by stirring under argon atmosphere for 1 hour. After a solution in THF (0.3 ml) of the [3a(R)]-1(R)-[1(S),5-dimethyl-5 -triethylsilyloxyhexyl]-7a(R)-methyl-4-oxo-octahydro-1H-indene (23.1 mg, 0.059 mmol) obtained in Reference Example 5 was added to the mixture, the reaction temperature was immediately raised to room temperature. After 1 hour, the mixture was diluted with n-hexane and filtered with silica gel; the filtrate was concentrated under reduced pressure. The resulting residue was purified by preparative TLC (n-hexane) to give the titled compound (10.0 mg, 38%) as a yellow oil.

$[α]_D^{23}$ +62.1° (c0.33, CHCl$_3$);

IR (neat) 1462, 1235cm$^{-1}$;

$^1$H NMR (200 MHz, CDCl$_3$) δ 5.64(br t, 1H, J=1.6 Hz), 2.86(br dd, 1H, J=9.2, 4.0 Hz), 1.20–2.10(m, 18H), 1.18(s, 6H), 0.94(t, 9H, J=7.9 Hz), 0.90(s, 3H), 0.56(s, 3H), 0.56(q, 6H, J=7.9 Hz).

Example 26

Synthesis of (5Z,7E)-(1R,2R,3R)-1,3-bis (t-butyldimethylsilyloxy)-2-(3-t-butyldimethylsilyloxypropoxy)-25-triethylsilyloxy-9,10-secocholesta-5,7,10(19)-triene

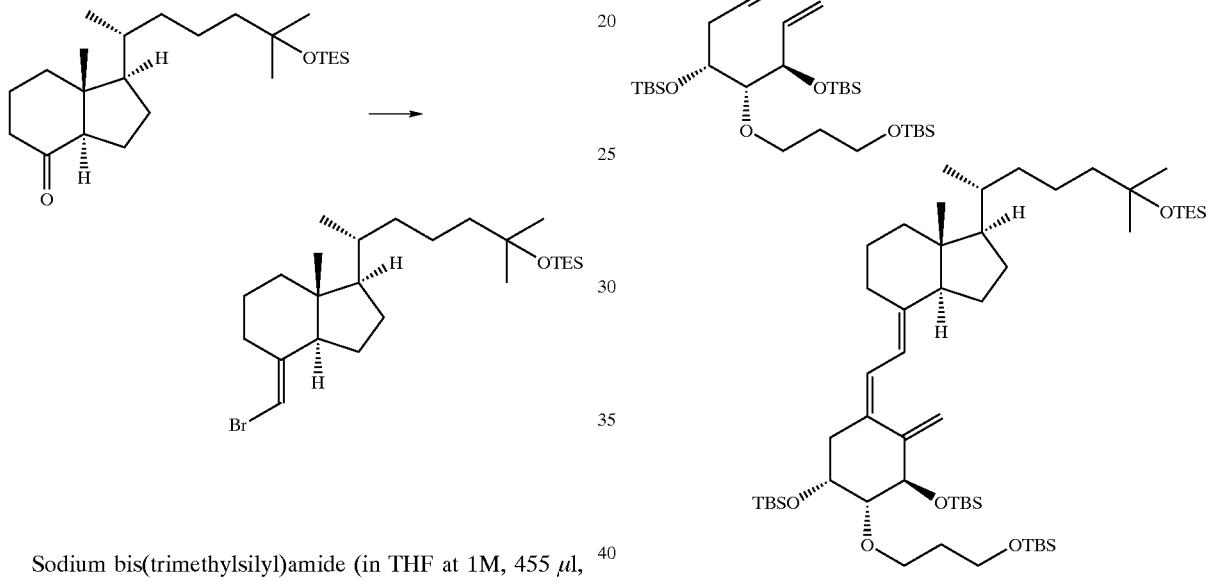

A mixture solution of triphenylphosphine (1.7 mg, 0.0065 mmol) and tris(dibenzylidene-acetone) (chloroform) dipalladium(0) (0.9 mg, 0.00087 mmol) in toluene (0.2 ml) and triethylamine (0.3 ml) was stirred at room temperature for 10 min. and then mixed with a solution in toluene (0.2 ml) of the [3a(R)]-4(E)-bromomethylene-1(R)-[1(S),5-dimethyl-5-triethylsilyloxyhexyl]-7a (R)-methyl-octahydro-1H-indene (10.0 mg, 0.021 mmol) obtained in Reference Example 6 and the 3(R)-3,5-bis( t-butyldimethylsilyloxy)-4-(3-t-butyldimethylsilyloxypropoxy)-1-octen-7-ine (8.2 mg, 0.015 mmol) obtained in Example 21, followed by heating under reflux for 4.5 hours. The resultant was diluted with n-hexane and filtered with silica gel; the filtrate was concentrated under reduced pressure. The resulting residue was purified by preparative TLC (n-hexane:benzene=2:1) to give the titled compound (3.5 mg, 26%) as a colorless oil.

$^1$H NMR (500 MHz, CDCl$_3$) δ 6.22(d, 1H, J=11.2 Hz), 6.00(d, 1H, J=11.2 Hz), 5.26(s, 1H), 4.98(d, 1H, J=2.7 Hz), 4.23(d, 1H, J=6.4 Hz), 4.18(m, 1H), 3.61–3.74(m, 4H), 3.23(br d, 1H, J=6.4 Hz), 2.81(d, 1H, J=11.8 Hz), 2.46(dd, 1H, J=13.0 Hz, 8.9 Hz), 2.21(dd, 1H, J=13.0 Hz, 3.4 Hz), 1.19–2.09(m, 32H), 0.88–0.97(m, 36H), 0.51–0.59(m, 6H), 0.04–1.00(m, 18H).

Test Example 1

Assay for Binding to Vitamin D Receptor (VDR)

By the radio receptor assay (RRA), compounds 1a and 1b of the present invention were tested for their ability to bind to vitamin D receptor derived from chick intestine.

$^3$H-1α,25-dihydroxyvitamin $D_3$ was dissolved in ethanol (20 μl) at a concentration of 10,000 dpm. Three test compounds, 1α,25-dihydroxyvitamin $D_3$, compound 1a and compound 1b, were diluted with ethanol to give concentrations in the range of from 1 to 100,000 nM, respectively.

To each of small tubes, 20 μl of $^3$H-1α,25-dihydroxyvitamin $D_3$ in solution and 50 μl of a test compound (i.e., 1α,25-dihydroxyvitamin $D_3$, compound 1a or compound 1b) in solution were added. A solution of vitamin D receptor was prepared by dissolving 25 mg of VDR in 70 ml of 0.05M phosphate buffer solution containing 0.3 M KCl and 5 mM DTT (dithiothreitol) and 0.5 ml of the resulting solution was added to each tube, followed by mixing. The resulting mixtures were incubated at 4° C. for 3 hours; each of them was mixed with 0.125 ml of dextran-coated charcoal (commercially available from YAMASA), incubated for 30 min. under ice cooling and centrifuged for 15 min. at 3000 rpm for B/F separation (separation of bound VDR (B) and free VDR (F)). To 0.5 ml of the supernatant, 5 ml of liquid scintillator was added for radioactivity measurement. The $B/B_0$ value was calculated from the measurements (B: radioactivity measured in the presence of a test compound, $B_0$: radioactivity measured in the absence of the test compound). The results are shown in FIG. 1.

As is apparent from FIG. 1, compound 1a and compound 1b show affinity for the vitamin D receptor.

The whole content of Japanese Patent Application No. 10-42295 on the basis of which the present application claims the priority is incorporated herein by reference.

INDUSTRIAL APPLICABILITY

The vitamin D derivatives of the present invention having the general formula (1) have physiological activities such as calcium metabolism-controlling activity and a differentiation-inducing activity on tumor cells, are expected to be useful as therapeutic agents for diseases associated with abnormal calcium metabolism, such as osteoporosis, osteomalacia, etc. and as an antitumor agent; in addition, they are regarded to be metabolites of vitamin D derivatives having a substituent at 2β position, particular, 2β-(3-hydroxypropoxy)-1α,25-dihydroxyvitamin $D_3$. Compounds having the general formulae (2), (3), (4) and (5) are useful intermediates for the synthesis of the compound of the present invention having the general formula (1) or various vitamin D derivatives having a hydroxy group at 24 position. Compounds of the general formula (5) can be also used as an intermediate for the synthesis of 2β-(3-hydroxypropoxy)-1α,25-dihydroxyvitamin $D_3$ having useful physiological activities.

What is claimed is:

1. A process for preparing vitamin D derivatives having the following formula:

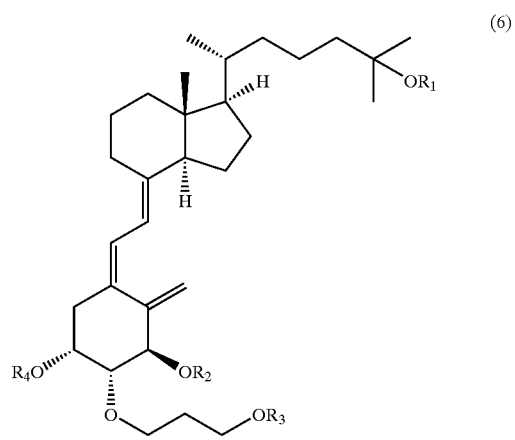

wherein $R_1$, $R_2$, $R_3$, and $R_4$, which may be the same or different, represent a hydrogen atom or a protecting group, comprising:
reacting a compound of formula (2)

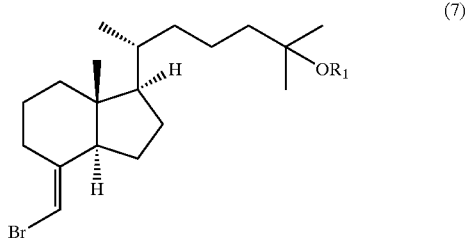

wherein $R_1$ represents a hydrogen atom or a protecting group, with a compound having the formula (3)

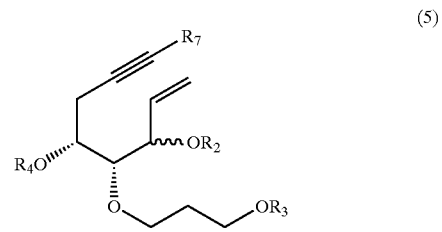

wherein $R_7$ represents a hydrogen atom and $R_2$, $R_3$, and $R_4$, which are the same or different, represent a hydrogen atom or a protecting group.

2. A compound of the formula (1):

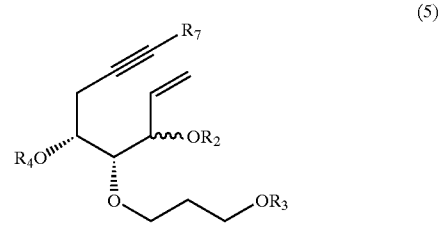

wherein $R_7$ represents a hydrogen atom and $R_2$, $R_1$, and $R_4$ represent a hydrogen atom or a protecting group.

* * * * *